United States Patent [19]
Myers et al.

[11] Patent Number: 5,849,223
[45] Date of Patent: Dec. 15, 1998

[54] LIQUIFLASH PARTICLES AND METHOD OF MAKING SAME

[75] Inventors: Garry L. Myers, Reston, Va.; Robert K. Yang, Flushing, N.Y.; Mark R. Herman, Nokesville, Va.

[73] Assignee: Fuisz Technologies Ltd., Chantilly, Va.

[21] Appl. No.: 453,053

[22] Filed: May 26, 1995

Related U.S. Application Data

[62] Division of Ser. No. 330,412, Oct. 28, 1994, Pat. No. 5,683,720.

[51] Int. Cl.$^6$ .................................................. A61K 9/14
[52] U.S. Cl. .................................. 264/15; 264/7; 424/489; 424/490; 424/493
[58] Field of Search .............................. 241/15; 424/489, 424/490, 493; 426/515, 512; 264/5, 7

[56] References Cited

U.S. PATENT DOCUMENTS

| | | |
|---|---|---|
| 3,686,000 | 8/1972 | Lawrence . |
| 3,758,678 | 9/1973 | Lindsay et al. ............................ 424/1 |
| 4,079,125 | 3/1978 | Sipos . |
| 4,323,523 | 4/1982 | Ueda et al. . |
| 4,808,413 | 2/1989 | Joshi et al. ............................ 424/458 |
| 4,876,094 | 10/1989 | Benton et al. . |
| 4,948,622 | 8/1990 | Kokubo et al. . |
| 4,971,805 | 11/1990 | Kitanishi et al. . |
| 5,055,306 | 10/1991 | Barry et al. . |
| 5,183,493 | 2/1993 | Brandau et al. ............................ 75/335 |
| 5,204,108 | 4/1993 | Illum . |
| 5,213,810 | 5/1993 | Steber . |
| 5,453,280 | 9/1995 | Moest et al. ............................ 424/458 |
| 5,464,632 | 11/1995 | Cousin et al. ............................ 424/465 |
| 5,549,917 | 8/1996 | Charukuri et al. ............................ 426/96 |
| 5,569,467 | 10/1996 | Ruiz ............................ 424/489 |

OTHER PUBLICATIONS

FMC Corporation, Pharmaceutical Division, Product Information Sheets on AviSphere$^{SM}$ System, AviSpheres™, Drug Loaded Spheres, Copyright 1993 FMC Corporation.

*Primary Examiner*—Jeffrey Mullis
*Attorney, Agent, or Firm*—Sandra M. Nolan

[57] ABSTRACT

The present invention is a method of making discrete particles by subjecting an organic feedstock to liquiflash conditions whereby the feedstock is transformed instantaneously from solid to liquiform to solid. Liquiform is a transient condition wherein the feedstock has substantially unimpeded internal flow. Shear force is imparted to the liquiform feedstock in an amount sufficient to separate tiny masses of feedstock. The tiny masses solidify as discretized particles. The present invention also includes unique products resulting from the process, e.g., a monodispersed microsphere product and coated particles prepared therefrom.

34 Claims, 19 Drawing Sheets

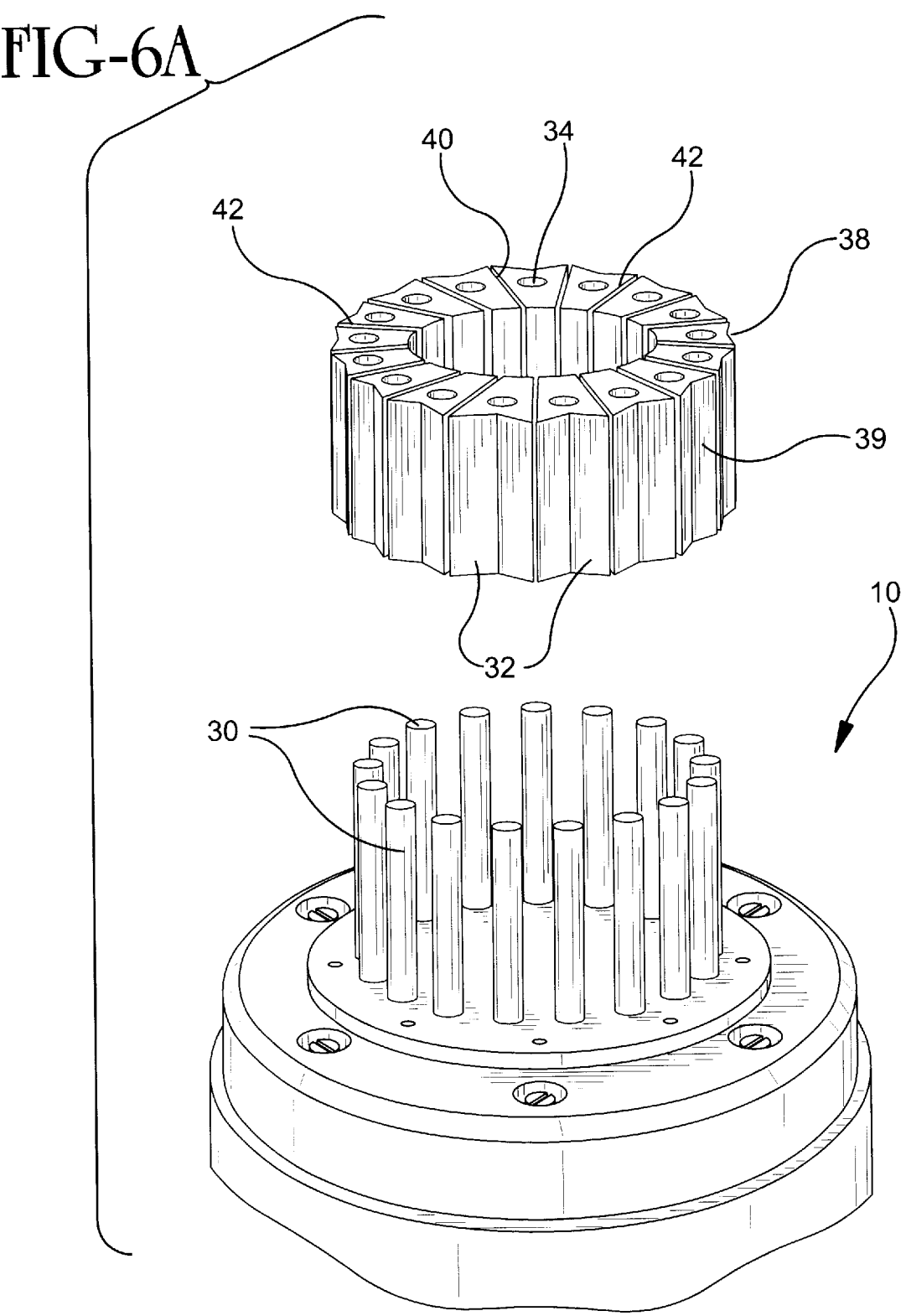

LIQUIFLASH PARTICLES AND METHOD OF MAKING SAME

Case in hand is a divisional application of U.S. application Ser. No. 08/330,412 filed on Oct. 28, 1994 now U.S. Pat. No. 5,683,720.

BACKGROUND OF INVENTION

The present invention relates to the art of processing material, and, in particular, to a method of harnessing natural mass formation forces, and the products resulting therefrom.

Over the years considerable time, energy and expense have been expended to devise methods for producing substances having unique morphologies in order to meet different requirements for utilizing a variety of substances. For example, it has been found that multiparticulates are useful in providing bio-availability of active ingredients to a host subject. Dosage units prepared from multiparticulates are able to introduce active ingredients in a form which a) disperses freely, b) maximizes absorption by increased surface area, while c) toxicity is minimized.

Within the last two decades, investigation in the area of multiparticulates has resulted in the development of spheroidal particles carrying active ingredients for delivery to a bio-system. This process, in general, will be referred to from time to time herein as spheronization. Spheronization has led to the develop of several technologies such as spherical agglomeration (e.g., balling, pelletizing), spray congealing, and cryopelletization.

For example, spherical agglomeration processes employ the uses of inclined dish pelletizers, rotary fluidized bed granulators, and marumerizers. Each of these systems rely primarily on liquid bridging and intermolecular and electrostatic forces for binding, often employing binding agents as a necessary part of the formulation. The dish pelletizing process has been found most useful for production of non-powder agglomerations. In order to produce powder agglomerations, a rotary fluidized bed granulator has been used. This process can produce particles which are smaller than that produced using a dish pelletizer.

In spray congealing processes, the drug or active ingredient can be melted or dispersed in hot melts of gums, waxes, fats, and other materials such as excipients. The molten mass is atomized using air, ultra-sound, or a spinning disk. Usually, this process results in a wide distribution of particle sizes, and care must be taken to obtain the correct range of sizes desired for the particular application. Spray congealing is not considered useful for preparing particulates which include heat sensitive drugs since the exposure to high temperature can be inimical to the stability and viability of the active ingredient.

Indeed, the need for preparing particulates which include heat sensitive active ingredients has led to another recent advancement of spheronization technology which is referred to as cryopellitization. Cryopellitization includes the dissolution or dispersion of a drug or active ingredient with water fillers and binders. The viscosity of the resulting dissolution system is very low. Consequently, the dissolution can be poured into liquid nitrogen and thereby form droplets as the dissolution system falls through the nitrogen. The droplets quickly freeze and are later lyophilized to produce fairly large bead like granules having a largest dimension (e.g., diameter) of 0.8 to 2.0 millimeters. While cryopellitization reduces the disadvantage of heat stress generally related to solvent-free products, disadvantages include cost of production, particle size, and output.

Yet another process, referred to as marumerizing is a method whereby a wet paste prepared from a drug or active ingredient, water and a binder is extruded through a screen to produce extrudate. The extrudate is chopped as it exits the extruder opening to produce rod-shaped particles. The rod-shaped particles are further shaped into spheroids using centrifugal and frictional forces provided by a rotating plate. Marumerizing suffers from several disadvantages including composition requirements, difficult and involved processing steps, and mechanical and electrical energy required to drive the processing equipment. Moreover, it is difficult to maintain a high degree of size and shape consistency by the marumerizing process.

None of the processes presently known in the art of particulate preparation have been able to take advantage (at commercial manufacturing volume) of natures ability to form masses of material with a high degree of consistency.

In commonly-owned copending application Ser. No. 08/269,679 filed Jul. 1, 1994 (now allowed), and its divisionals, U.S. Pat. No. 5,549,917 issued Aug. 27, 1996 and U.S. application Ser. No. 08/269,780 filed Apr. 9, 1996, (the contents of which are incorporated herein by reference), a method of forming a solloid is disclosed. The solloid formation procedure involves feeding a composition, which includes an active-bearing non-fat substrate and a solid fat at room temperature, preferably to an extruder, subjecting the composition to flash flow conditions, and expelling the composition in a flowable state while applying disruptive force to the composition to form discrete solids. The method includes a carrier element in which an active ingredient is carried.

It is, therefore, an object of the present invention to provide a highly efficient and predictable means for naturally forming minute masses of material on a commercial scale. Other and further objects of the present invention will be realized by those skilled in the art in view of the disclosure set forth herein.

SUMMARY OF THE INVENTION

The present invention includes a method of making discrete particles by subjecting a solid organic feedstock, capable of being transformed to a liquiform in the substantial absence of a dissolving medium, to liquiflash conditions to provide substantially unimpeded internal flow. The feedstock, thus reduced to unimpeded internal flow, is subsequently discretized by natural mass separation of the flowing feedstock in the presence of shear force to form shearlite particles, i.e., particles which appear as shearform pearls.

The present invention also relates to a new method of providing a substrate, i.e., shearlite particles, for the purpose of coating. Shearlite particles prepared in accordance with the present invention are ideally suited for coating. The highly consistent spheroidal shape and the narrow range of size distribution causes the shearlite particles to flow evenly and easily and to be susceptible to even coating with a minimum amount of coating material. Consequently, shearlite particles can be efficiently coated to obtain a corresponding consistently coated product.

The shearlite particles herein can be a non-active substrate, such as sugar (see Example 1), or an active substrate, e.g., analgesics, non-steroidal anti-inflammatory agents, etc. In any event, coatings may be applied thereto in a highly efficient method to obtain the desired results. Thus, when the shearlite particles are a non-active substrate coatings include, but are not limited to, active ingredients, controlled-release agents, taste-altering ingredients, e.g., flavors, antidotes, muco-adhesives, fats, emulsifiers, polymers, etc., and mixtures thereof.

"Liquiflash conditions" as used herein means those conditions which provide transformation of a solid to a liquid state and then to the solid state (e.g., solid-liquid-solid) instantaneously. By instantaneously is meant less than seconds, in most cases on the order of fractions of a second, most preferably milli-seconds. Thus, certainly the transformation from solid to liquid to solid takes place in a time period of less than five seconds, preferably less than one second, and most preferably less than 0.1 seconds.

During this rapid transition, shear forces can act on the material to discretize the feedstock. Thus, liquiflash conditions are the combination of temperature and force which induce an organic feedstock to flow and re-solidify into a changed shape as it is being discretized by the action of shear force. In preferred embodiments the size and the new shape are highly consistent among the discretized particles. Thus, the shape is preferably spheroidal and the size distribution is very limited with only minor variations.

As a result of the process of the present invention, the discrete particles produced are preferably microspheres, which as used herein, preferably means not greater than about 500 $\mu$m, more preferably not greater than about 400 $\mu$m, and most preferably not greater than about 300 $\mu$m. In the preferred method of the present invention the liquiflash conditions are provided by a spinning head having a heated peripheral barrier with exit openings provided therethrough for passage of feedstock flowing under centrifugal force. The shear force referred to above is imparted to flowing feedstock by resistance of ambient atmosphere against the liquiform feedstock as it exits the spinning head.

The ambient atmosphere can be undisturbed except by the motion of the spinning head. Alternatively, the ambient atmosphere about the spinning head can be a positive counter or concurrent flow adjacent the outside surface of the processing barrier. This permits greater control of discretization of liquiform feedstock.

The discretized particles separated from the mass of flowing feedstock are cooled. In a preferred form of the present invention the discretized particles are monodispersed. "Monodispersed" as used herein refers to the production of a plurality of uniform spherical particulates, e.g., shearlites. As explained hereinabove methods for barrier processing of feedstock known in the art generally results in a product having a wide variety of sizes and shapes. This is due to many factors all of which contribute to a basic lack of control over the formation of particulates.

In the present invention, however, natural mass forming forces available in minute material masses, e.g., entropy, et al., provide a predictable uniform size. Thus, monodispersed means that at least about 40% by weight, preferably at least about 60% by weight and most preferably at least about 80% of the product herein have a largest diameter which is within 60% of the mean particle diameter. Particle diameter is the dimension which is the greatest straight line dimension in the largest plane taken through a three dimensional particulate. Generally, when the particulate is spheroidal in shape, the particulate diameter is the diameter of the spheroid. In a preferred embodiment, monodispersability means that at least 40% of the particulates are within 50% of the mean particulate diameter, and, in a most preferred embodiment, within 40% of the mean particulate diameter.

Processable feedstock materials used in the present invention are predominantly "organic material." Organic material as used herein means carbon containing compounds, e.g., composition and structure of carbon containing compounds, whereas inorganic materials (or compounds) pertain to substances which do not contain organic type carbon. Polycarbon carbon compounds are preferably used in the present invention. Hydrocarbons are a major portion of organic materials, and are also preferred for use herein. Metals, inorganic carbonates and silicates, e.g., glass, are not considered organic materials for purposes of the present invention. Furthermore, proteinaceous material having high molecular weight is not considered "organic material" as used herein.

In a preferred embodiment of the present invention, the feedstock material includes a medicament so that the resulting product can be a delivery system for inclusion in a dosage unit.

Another preferred embodiment is a sucrose product having a highly consistent small size and spheroidal shape. The size range is from 5 $\mu$m to 100 $\mu$m, and is preferably from 10 $\mu$m to 50 $\mu$m—ideally 15$\mu$–30$\mu$, centered around 25 $\mu$m. This product is very useful in a chocolate product because of the ability to reduce the fat content of the chocolate. Thus, a low fat chocolate product made from highly uniform sucrose shearlites having a size range centered at about 25 $\mu$m is also contemplated in the present invention.

The present invention also includes the discrete particles formed by the process herein.

Another preferred embodiment is a discrete particle consisting of a medicament which has a solid spherical body having substantially no discontinuity therein. Consequently, the spherical body can be a substantially pure drug or active ingredient which is at least 80% of the theoretical density of the drug at standard temperature and pressure, and is preferably at least 90%, and most preferably not less than 95% theoretical density.

Preferably, the spherical body or bodies are microspheres as defined herein. As a result of the present invention drugs or combinations of drugs can be combined with excipients and prepared on a commercial scale to provide spherical particles having a high degree of size consistency. This capability provides a major advantage in the art of preparing sustained released delivery systems.

The product of the present invention can be a true amalgam of different drugs or active components or combinations of amalgams and mixtures of drug and non-drug ingredients. If two or more drug components included in the feedstock have similar melting points, the product will usually be a true amalgam of the drug components. If one or more of the active has a higher melting point than one or more of the other components, the higher melting drug will disperse substantially consistently throughout the liquiform when the lower melting point ingredients are processed. Finally, one of the components, such as the low melting point ingredient, can be a non-active ingredient. For example, sucrose can be used in combination with active ingredients to form a non-dispersed spherical particulate product having an active ingredient substantially evenly distributed throughout. One particularly useful combination of active agents includes agents used as cough and cold treatment.

The product of the present invention can also be used as a substrate on which a substance can be deposited to remove toxins from a bio-system. Since the present product is an excellent delivery vehicle for a bio-system, a substance which removes, for example, toxins, can be deposited thereon. The deposited substance can be an adsorbent or absorbent which acts mechanically, chemically, or biologically to extract an unwanted agent from the bio-system, e.g., the human body. Such substance can be psyllium, epichlorhydrin, or a biological conjugate, etc.

A further advantage of the present invention, includes the ability to produce a particle size in the range of up to about 500 $\mu$m with a high degree of consistency on a commercial manufacturing scale. Once again, the spherical shape of the particles and narrow particle size range enhances the ability to provide even dissolution and, consequently, predictable bio-availability.

Yet another aspect of the present invention takes advantage of the ability to coat the spherical particles with an even coating. An even coating is highly desirable for the purpose of providing controlled release of drugs or active ingredients. Such coating capabilities also enhance the ability to taste mask otherwise unpalatable active ingredients. The highly predictable tiny spherical particles enables the practitioner to obtain a thin uniform coating and impart better mouthfeel and taste to the user.

The present invention also includes a method of making coated discrete particles which includes providing at least one coating to a discrete particle prepared by liquiflash processing. The discrete particles are prepared by subjecting a solid, organic feedstock to liquiflash conditions and separating discretize particles therefrom. The present invention also provides for the product resulting from coating such particles.

In preferred embodiments of this aspect of the invention, the feedstock can be a saccharide based material, preferably, a sugar. Alternatively, the feedstock material can itself be a medicament which includes one or more active agents.

The coating or coatings can be selected from the group consisting of a medicament, an antidote, a controlled-release substance, a taste-altering substance, and combinations thereof. In one preferred embodiment of the present invention, the coating includes at least one or more fats, emulsifiers, and combinations thereof.

The medicaments contemplated for use in this aspect of the invention include one or more active agents as set forth hereinbelow. Controlled-release substances are those which are known in the art, some of which have been set forth with specificity in the present disclosure. Taste-altering substances include taste-masking substances, sweeteners, flavorings, and, in general, any substance which changes the natural organoleptic perception of the product resulting from the liquiflash processing.

In a further preferred embodiment of the present invention, the medicament includes an anti-inflammatory substance which is a non-steroidal anti-inflammatory agent selected from the group consisting of tenidap, oxicams and derivatives of salicylic, acetic, propionic, and fenamic acid. A particularly preferred non-steroidal anti-inflammatory agent is ibuprofen which is a propionic acid anti-inflammatory agent. Other propionic acid anti-inflammatory agents includes flurbiprofen, naproxen, and ketoprofen.

In yet another preferred embodiment of the preferred embodiment of the present invention, the medicament includes H$_2$-antagonists as an active agent.

A further aspect of the present invention is a method of improving the flow characteristic of material by subjecting it to liquiflash conditions to provide highly uniform substantially spheroidal discretize particles in accordance with the present invention. The flow property of a substance as used herein means the ability of the substance to flow. A mass of material can be made to flow by tilting the surface on which a quantity of the material rests until it moves under the force of gravity in a direction away from the "at rest" position. A substance with good flow properties will move easily and evenly away from the "at rest" position. Such a material is easily utilized in processing apparatus for preparing compressed tablets, capsules, etc. Substances without good flow properties, do not readily flow, and generally do not move in an even condition. Such substances generally are transported in the form of clumps or uneven masses from the "at rest" position.

In one most preferred embodiment of the present invention, it is contemplated that the substrate and coatings thereover will be provided with active agents to provide a cough and cold treatment. Such cough and cold combinations include, but are not limited to pseudoephedrine, chlorpheniramine, diphenhydramine, dextromethorphan, and analgesics.

Highly uniform spheroidal morphology resulting from the present invention improves the ability to direct the flow of ingredients into tableting machinery and for the purpose of filling capsules. For example, when ascorbic acid is prepared in a highly consistent spheroidal particulate in accordance with the present invention, the resulting product can be directly tabletted. On the other hand, ascorbic acid not prepared in accordance with the present invention is not directly tablettable.

Other applications include the ability to load non-drug materials on to or into spherical particles such as laundry enzymes into saccharides, or to combine different drugs or different families of drugs into a single spherical particle. Inasmuch as the particles are predictably highly uniform, simple mixing ensures drug uniformity as well as delivery uniformity.

Particulate products can be produced on a commercial scale for several applications such as industrial and food uses. Sugar microspheres can be manufactured and used as a support for coating with, for example, polyvinyl alcohol (Elvanol™). Sugar or starch microspheres can be used as support or substrates for stabilizing enzymes and to prevent dusting, e.g., elimination of dust resulting handling of enzyme-containing material.

Examples of other industrial chemicals which can benefit from less dusting and better flow property afforded by the present invention include, but are not limited to phenol, styrene, butylated hydroxy anisole (BHA), tert butylhydroxy hydroquinone (TBHQ), hydroquinone, insecticides, herbicides, combinations of insecticides and herbicides, antifungals. There are many other such chemical substances which present damages from explosion and/or personal contact. The present invention includes processing all such substances under liquiflash conditions and/or coating as an aspect of the invention.

Other and further advantages of the present invention will be realized by those skilled in the art in view of the disclosure set forth herein, and it is intended to include all such advantages as part of the present invention, and to be included within the scope of the claims appended hereto.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein:

FIGS. 6A and 6B depict another apparatus used in the process of the present invention;

DETAILED DESCRIPTION OF THE INVENTION

Figure 1A:
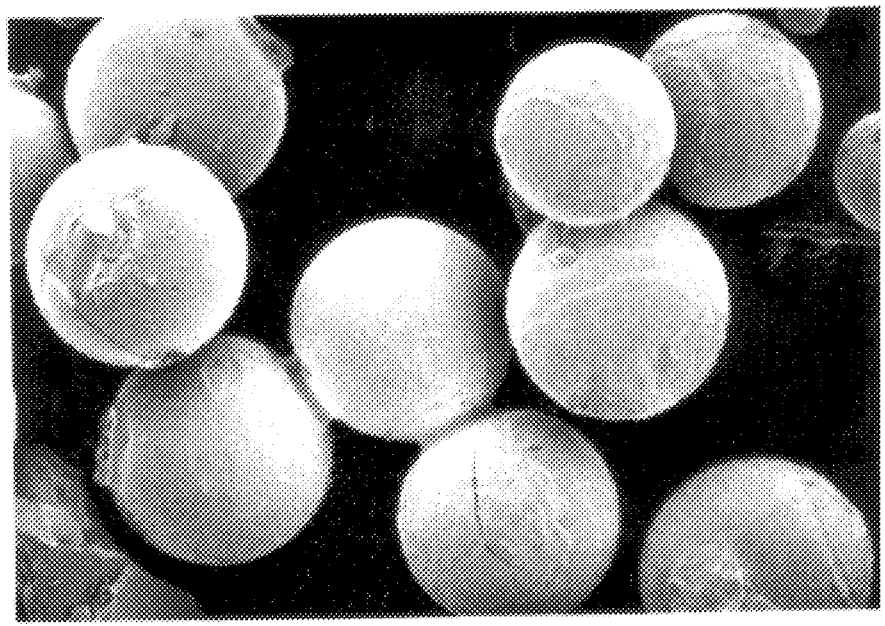
FIGS. 1A, 1B, and 1C are photomicrographs of acetaminophen before and after processing in accordance with the present invention.

The present invention includes a method of making discrete particles of material by harnessing nature's mass forming capability. Just as forces existing between and within material masses have formed countless spheroidal bodies existing throughout the universe, so to have the inventors herein harnessed natures tendancy to provide optimum mass for minimum surface area by instantaneous transformation from solid to liquiform to solid.

The method of the present invention is implemented by subjecting a feedstock capable of being transformed to liquiform in the absence of a dissolving medium to liquiflash conditions to provide substantially unimpeded internal flow. The feedstock contemplated for use in the present invention is a feedstock which is capable of being transformed instantaneously from a solid to a liquid and back to a solid.

It has become known to those skilled in the art of material processing, and, especially to artisans familiar with the technology of the owner of the present invention, that "flash flow" refers to conditions of temperature and force required to transform a solid feedstock to a new solid having a different morphology and/or chemical structure in the absence of a heat history. Flash flow can be implemented by "flash heat" processing. The term flash heat is understood to mean a process which includes subjecting the feedstock to combinations of temperature, thermal gradients, flow, flow rates and mechanical forces of the type produced in the machines referred to herein. The term "flash flow" is described in the co-owned U.S. Pat. No. 5,236,734 issued Aug. 17, 1993, U.S. Pat. No. 5,238,696 issued Aug. 24, 1993, and co-pending U.S. application Ser. No. 07/787,254 filed Nov. 4, 1991 (now abandoned), and U.S. application Ser. No. 07/893,238, now U.S. Pat. No. 5,518,730 issued May 21, 1996, the contents of which are incorporated herein by reference.

Flash flow processing known to the art to date contemplates transformation of feedstock material substantially immediately upon reaching a flow condition whereby the material can move at a subparticle level. Liquiflash processing, however, contemplates the reduction of the feedstock material under conditions of heat and pressure to a condition wherein any resistance to liquid flow, e.g., viscosity which impedes the propensity to form liquid droplets, is eliminated. On a macro scale, this condition appears to provide a liquid or liquiform, which terms are used interchangeably herein.

With liquiflash processing, once the feedstock is reduced to a condition wherein substantially all resistance to liquid flow is removed, shear force is imparted to the flowing feedstock in an amount sufficient to separate individual or discrete particles from the mass. The particles produced by this separation process, referred to herein as discretization, have a size and shape influenced only by the natural mass separation of the flowing feedstock in the presence of the impinging shear force. The particles thus formed can be referred to as shearlite particles or particulates, e.g., shearform pearls. If the impinging force is such that the separation created is that of a continuous stream, discretization has not occurred.

Moreover, the feedstock contemplated for use herein must be capable of undergoing the required transformation without substantial and preferably no significant deterioration of the material present therein.

It has been found that liquiflash conditions and the subsequent shear force imparted thereto in the method of the present invention can be provided by "barrier processing" which is closely akin to flash heat processing as described herein. The flash heat process is a process wherein feedstock can be introduced to a "cotton candy" fabricating type machine. The spinning machine used to achieve a flash heat process can be a cotton candy type machine such as the ECONO FLOSS Model 3017 manufactured by GOLD METAL PRODUCTS COMPANY of Cincinnati, Ohio. Machines useful in the process of the present invention can be found in co-pending U.S. application Ser. No. 954,257 filed Sep. 30, 1992, which has issued as U.S. Pat. No. 5,427,811 to Fuisz, et al. on Jun. 27, 1995 (incorporated herein by reference), and co-pending U.S. application bearing Attorney Docket No. 447-119, bearing title U.S. application Ser. No. 08/330,938 filed Oct. 28, 1994, issued as U.S. Pat. No. 5,458,823 to Perkins, et al. on Oct. 17, 1995 (also incorporated herein by reference).

However, in order to implement the liquiflash process as required in the present invention, the flash heat apparatus and process have been modified. In particular, modifications have been made to deliver sufficient energy to the point of transformation of the feedstock, e.g., the barrier of the spinning head, to liquify it instantaneously.

Considerations for successfully carrying out the objects of the present invention reside in the appropriate combination of the following features:

I. spinner head;
II. liquiflash conditions of temperature and centrifugal force;
III. the character and size of the barrier; and
IV. the character of the ambient conditions adjacent the spinner head.

Spinner heads may be adapted to produced microspheres. In general, some of the spinner heads presently available can be modified to provide sufficient energy to the feedstock so that in the presence of appropriate centrifugal force the feedstock transforms to liquiform and is processed substantially instantaneously. Gas (air) resistance discretizes the feedstock. Elements identified hereinabove can be adjusted to optimize discretization for a particular feedstock.

In order to deliver sufficient energy to achieve liquiflash conditions, the inventors herein have devised configurations of equipment in which the heat delivered to the barrier is increased. This requirement has been achieved in apparatus disclosed in co-pending Application bearing U.S. application Ser. No. 08/330,938 filed Oct. 28, 1994 issued as U.S. Pat. No. 5,458,823 to Perkins, et al. on Oct. 17, 1995 which are incorporated herein by reference. For example, the number of individual heaters at the periphery of the spinning head can be increased. Another way of increasing the thermal energy delivered to the feedstock is by providing a tortuous path which retards movement of feedstock through the barrier on the periphery of the spinning head. Those skilled in the art will appreciate that the combination of increasing the delivery of heat and retarding flow of feedstock can be combined by various design features to obtain optimum results in the process and, consequently, the product. As indicated above, it is intended to cover all such variations of control over the delivery of heat and the rate of passage of the feedstock through the barrier as a means of providing liquiflash conditions.

It is preferred that the surface of the spinner head which contacts the feedstock be coated with a low free surface energy substance. For example, a Teflon® based coating will reduce friction between the feedstock and the surface of the spinner head as the feedstock travels towards the processing boundary and is forced thereagainst.

Referring to FIGS. 2A, 2B and 2C, the unique phenomenon of liquiflash is schematically depicted. Centrifugal force created in the spinning head flings the feedstock F to the barrier found at the periphery of the spinning head. Heating elements H provided at the periphery reduce the feedstock to a liquiform condition wherein internal flow becomes unimpeded.

In this liquiform condition, centrifugal force moves the feedstock through the openings O provided in the peripheral barrier so that the liquid is exposed to shear force provided by the ambient atmosphere found immediately outside the head. It is believed that the flowing feedstock creeps as a layer along the surface of the exterior of the head until a sufficient volume is built up in the laminar flow whereby a tiny mass m of liquiform feedstock begins to form a generally deformed drop, e.g., a teardrop shape, T, which is met by the atmosphere surrounding the spinning head. The shear force imparted on the teardrop T being formed by the flowing feedstock separates a droplet D as a discrete particle by natural mass separation. Natural mass separation at this point is the combination of weight, internal cohesive intra- and intermolecular forces present in the liquiform feedstock and adhesive forces between the liquiform feedstock and the exterior surface of the spinning head. Inasmuch as there is a continuous flow of feedstock, the teardrops are continuously formed and separated as discretized particles D or shearlite particles.

The centrifugal force imparted to the teardrops flings the discretized particles into the surrounding atmosphere to permit formation of discrete solid particles D. As a consequence of this unique process the discrete particles formed thereby have been found to be highly uniform microspheres, i.e., pearl like spheres having a size of not greater than 500 μm, and in most cases having a magnitude of between 25 and 300 μm.

Moreover, the discretized particles produced as a result of this process have been found to have a high degree of purity. Thus, drugs which are processed in the absence of any additives whatsoever have been found to experience a change in morphology which makes them ideal for predictable drug delivery systems. The drug product can be introduced into a formulation as highly uniform spheroids, or can be coated with delivery ingredients, taste masking ingredients, taste modifiers, dissolution retardants, dissolution expedients, etc.

It is also contemplated that the force required to separate the discretized particles can be varied by modifying the atmosphere surrounding the spinning head. For example, the apparatus can be operated in a chamber having multiples of atmospheric pressure, or virtually no pressure.

The conditions of liquiflash, i.e. principally temperature and centrifugal force, must be carefully controlled so that on melting to a degree that permits centrifugal force to move the liquiform material to and through the exit orifices, can be accomplished. To obtain this with pure compounds the operator can be guided by its known melting point. With mixtures of materials test melting points can be obtained as a rough guide before starting a run. With little experimentation, heater resistance power can be slowly supplied to a spinner head containing the material to be converted into microspheres and simultaneously the rate of spinning of the head can be increased until liquiflash conditions are met. The appearance of microspheres of the desired size range verifies that the optimum liquiflash conditions have been met for this particular material. For instance in Example II, set forth below, acetaminophen powder m.p. 169°–170.5° C., was employed in the described apparatus and the heat was progressively increased toward the melting point of the powder while the spinner head increased to about 3600 rpm. Upon melting, and when spheres in the size range of up to 420μ appeared, this constituted the optimum liquiflash conditions for this size range microspheres of acetaminophen.

Feedstock which is contemplated for use herein includes saccharides especially sugars, such as sucrose, and medicaments which can include active agents alone or in combination with other active agents or other ingredients. Quite surprisingly, saccharides and drugs can be processed without deterioration.

Medicaments which can be used in the present invention are varied. A non-limiting list of active agents which can be included in medicaments herein is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithromobotic drugs, hypnotics, antiemetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof. Other active ingredients contemplated for use in the present invention are $H_2$-antagonists.

Antacids are not considered candidates for liquiflash processing, but are contemplated for use in combination with other active or non-active organic feedstock materials which are capable of liquiflash processing. For example, calcium carbonate ($CaCO_3$), alone or in combination with magnesium hydroxide and/or aluminum hydroxide, can be included with other feedstock used as a carrier. Thus, antacids can be used in combination with $H_2$-antagonists, ibuprofen, ketoprofen, etc., which are capable of undergoing liquiflash processing.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate magnesium aluminate sulfate, magaldrate magnesium aluminosilicate, magnesium carbonate, magnesium glycinate, magnesium hydroxide, magnesium oxide, magnesium oxide, magnesium trisilicate, milk solids, aluminum mono-odibasic or mono-dibasic calcium phosphate, tricalcium phosphate, potassium bicarbonate, sodium tartrate, sodium bicarbonate, magnesium aluminosilicates, tartaric acids and salts.

Analgesics include aspirin, acetaminophen, and acetaminophen plus caffeine.

Other preferred drugs or other preferred active ingredients for use in the present invention include antidiarrheals such as immodium AD, antihistamines, antitussives, decongestants, vitamins, and breath fresheners. Also contemplated for use herein are anxiolytics such Xanax; antipsychotics such as Clozaril and Haldol; non-steroidal anti-inflammatories (NSAID's) such as Voltaren and Lodine; antihistamines such as Seldane, Hismanal, Relafen, and Tavist; antiemetics such as Kytril and Cesamet; bronchodilators such as Bentolin, Proventil; antidepressants such a Prozac, Zoloft, and Paxil; antimigraines such as Imigran, ACE-inhibitors such as Vasotec, Capoten and Zestril; anti-Alzheimer agents, such as Nicergoline; and $Ca^H$-Antagonists such as Procardia, Adalat, and Calan.

The popular $H_2$-antagonists which are contemplated for use in the present invention include cimetidine, ranitidine hydrochloride, famotidine, nizatidine, ebrotidine, mifentidine, roxatidine, pisatidine and aceroxatidine.

Another aspect of the present invention is a new particulate resulting from providing a substrate in combination of at least one coating. The substrate can either be a non-active ingredient such as a saccharide based material, preferably a sugar such as sucrose, or the substrate can be an active agent, or a combination of active agents. Thus, in one manifestation of this aspect of the invention the substrate can be sugar shearlite particles such as those produced in Example I hereinbelow. Drugs can then be coated thereover either alone or in combination with other types of coating materials. Further coatings can be added as desired. Alternatively, the shearlite particles themselves can be an active ingredient or a combination of active ingredients such as those discussed above with respect to the formation of amalgams. As a result of the narrow size range and the unique and reproducible shape of the particle, coating material can be deposited highly efficiently as very thin even coatings. Consequently, the desired effects such as time-release, flavor enhancement or alteration, can be achieved economically and efficiently.

In one specific embodiment of the present invention, the shearlite particles can be designed to deliver an active ingredient and an antidote. For example, a shearlite particle can be prepared from either an antidote or a non-active ingredient. If the particle is an antidote, it can be coated with an active ingredient. If the particle is made from a non-active ingredient, it can be coated with an antidote and subsequently again coated with an active ingredient. In either case a controlled-release coating can be provided thereover and/ or interspersed between coatings. Furthermore, another coating such as a muco-adhesive can be deposited to ensure that the active ingredient is delivered to the desired part of the body.

A further preferred embodiment of the present invention includes providing combinations of active ingredients which are designed as a cough and cold treatment. Thus, for example, two or more actives can be included in the feedstock to form an amalgam which can then be coated as desired for taste alteration and/or controlled-release. Alternatively, the cough and cold active ingredients can be provided in one or more of the substrate and the layers deposited thereover.

"Controlled-release" is used herein to describe a method and composition for making an active ingredient available to the biological system of a host. Controlled-release includes the use of instantaneous release, delayed release, and sustained release. "Instantaneous release" is self-explanatory in that it refers to immediate release to the biosystem of the host. "Delayed release" means the active ingredient is not made available to the host until some time delay after administration. (Dosages are usually administered by oral ingestion in the context of the present invention, although other forms of administration are not precluded from the scope of the present invention). "Sustained Release" generally refers to release of active ingredient whereby the level of active ingredient available to the host is maintained at some level over a period of time. The method of effecting each type of release can be varied.

The patent and scientific literature is replete with various sustained release (SR) methods and formulations. For common methods of obtaining SR systems, see *Sustained and Controlled Release Drug Delivery Systems,* Robinson, Joseph R., Ed., PP 138–171, 1978, Marcel Dekker, Inc. New York, N.Y. SR can be effected by use of coatings which include gels, waxes, fats, emulsifiers, combination of fats and emulsifiers, polymers, starch, etc.

Conventional SR formulations are generally designed to release their actives over an extended period of time, usually 8–24 hours. Conventional SR formulations use waxes or hydrophilic gums to prolong the release of the active ingredients. Conventional waxes and waxy materials used in pharmaceutical formulations are carnauba wax, spermaceti wax, candellila wax, cocoa butter, cetosteryl alcohol, beeswax, partially hydrogenated vegetable oils, ceresin, paraffin, myristyl alcohol, stearyl alcohol, cetylalcohol and stearic acid. They are generally used in amounts of about 10 to about 50% by weight of the total formulation.

Hydrophilic gums have also been known to be reasonably effective as SR carriers for both high-dose and low-dose drugs. Typical hydrophilic gums used as SR carrier materials are acacia, gelatin, tragacanth, veegum, xanthin gum, carboxymethyl cellulose (CMC), hydroxypropyl methyl cellulose (HPMC), hydroxypropyl cellulose (HPC) and hydroxyethyl cellulose (HEC). Generally these materials are present in amounts of about 10 to 50% by weight of the final formulation.

Starch USP (potato or corn) can be used as a component in controlled-release formulation. It generally functions in conventional applications as a diluent or as a disintegrant in oral dosage forms. Starch paste is also often used as a binder in these products. Various modified starches, such as carboxymethyl starch currently marketed under the trade name Explotab or Primojel are used as disintegrating agents. The literature discloses that native and modified starches are useful in promoting rapid release of drugs from solid oral dosage forms.

In all controlled release technologies it is desirable to be able to incorporate the active ingredient in its controlled-release pattern in a single dosage unit without deteriorating the active ingredient. Moreover, the dosage unit should be able to deliver the system without interfering with its release pattern.

Polymers are quite useful as coatings in the present invention. Solution coatings and dispersion coatings can be used to coat the shearlite particles. Plasticizers are also normally included in both organic solvent systems and aqueous systems. Some polymers useful for coating include, but are not limited to, the following: methylcellulose (Methocel® A made by Dow Chemical), hydroxypropyl methylcellulose (Methocel E provided by Dow Chemical or Pharmacoat® provided by Shin Etsu), ethyl cellulose, cellulose acetate, cellulose triacetate, cellulose acetate butyrate, cellulose acetate phthalate, cellulose acetate trimellitate (provided by Eastman Kodak), carboxymethylethyl cellulose (Duodcel®/Freund), hydroxypropyl methylcellulose phthalate, polymethacrylic acid-methacrylic acid copolymer (Type A 1:1 Eudragit L100; Type B 1:2 Eudragit S100; and Type C 1:1 Eudragit L100-55, aqueous dispersion 30% solids, Eudragit L30D), poly(meth)acryl ester: poly(ethyl acrylate, methyl methacrylate 2:1), Eudragit NE30D aqueous dispersion 30% solids, polyaminomethacrylate Eudragit E100, poly(trimethylammonioethyl methacrylate chloride) ammoniomethacrylate copolymer, Eudragit RL30D and Eudragit RS30D.

Plasticizers used in the above solvent plasticizers which may be used in the present invention are as follows: diethyl phthalate, dibutyl phthalate, triethyl citrate, glycerol triacetate, and dibutyl sebaccate.

Aqueous polymeric dispersions useful for coating the present invention include Eudragit L30D and RS/RL30D, and NE30D, Aquacoat brand ethyl cellulose, Surelease brand ethyl cellulose, EC brand N-10F ethyl cellulose, Aquateric brand cellulose acetate phthalate, Coateric brand Poly(vinyl acetate phthalate), and Aqoat brand hydroxypropyl methylcellulose acetate succinate. Most of these dispersions are latex, pseudolatex powder or micronized powder mediums.

Plasticizers which can be used for aqueous coatings include, but are not limited to, the following: propylene glycol, polyethylene glycol (PEG 400), triacetin, polysorbate 80, triethyl citrate, diethyl d-tartrate.

For example, enteric coatings broadly can include a porous film of cellulose acetate phthalate (provided by Eastman Kodak) in combination with beeswax for blocking its pores. Other combinations include shellac and ethyl cellulose mixtures, and shellac, methyl alcohol and castor oil mixtures. Also an ethylene-vinyl acetate copolymer can be used, such as duPont ELVAX 40.

Enteric substances used for in the present invention as a coating are polyacrylate substances bearing many carboxyl groups in their molecules. Examples are methacrylic acids-ethyl acrylate copolymers [manufactured by Rhom-Pharma Co. (West Germany) Eudragit® L300D], methacrylic acid-methyl methacrylate copolymer (Eudragit® L or Eudragit®S), hydroxy propyl methyl cellulose phthalate (manufactured by Shin-Etsu Chemical Co., HP-50, HP-55, HP-55S), hydroxypropyl methyl cellulose acetate phthalate (manufactured by Shin-Etsu Chemical Co., AS-LG, AS-LF, AS-MG, AS-MF, AS-HG, AS-HF), carboxymethyl ethyl cellulose [manufactured by Freunt Industry Co. (Japan)], cellulose acetate phthalate, and vinyl methyl ethermalic anhydride copolymer [manufactured by GAP Co. (US), AN-139, AN-169].

Preferably, Eudragit® L, Eudragit® S and HP 55 are employed, because they have high contents of carboxyl groups with high safety.

In general, processes known in the art for preparing coated particles can be used. For example, process for preparing particles as disclosed in U.S. Pat. No. 4,971,805 are contemplated for use with the shearlite particles. These processes are incorporated herein by reference and the disclosure set forth in the '805 patent is specifically incorporated herein by reference. See also U.S. Pat. No. 4,948, 622 to Kokubo, et al. which is incorporated herein by reference.

In the Kokubo, et al. '622 patent, the granules, beads and tablets were coated with a dispersion of cellulose ether and then subjected to wax treatment with heating to form a masking layer of wax. It is also contemplated to use waxes as a coating material in the present invention. As previously mentioned waxes include carnauba, beeswax, vegetable waxes, animal waxes (spermaceti) and synthetic wax such as carbowax, e.g., polyether. Also contemplated for use herein includes hydrocarbon waxes such as paraffins and petrolatums. Higher alcohols such as cetyl alcohol and stearyl alcohol, higher fatty acids such as stearic acids, esters of higher fatty acids, fatty acids esters of glycerins such as beaf tallow, lard, hardened soybean oil and hardened castor oil and polyethylene glycols such as PEG-6000 and PEG-20, 000 as well as various commercial products sold under the trade names of Lubri Wax—100 prectrol, which is a mixture of mono-,di-and tripalmitates of glycerin, and the like. These wax materials can be used either singly or as a mixture of two kinds or more according to the need.

The present invention also contemplates the use of fats in the coatings in the products produced by the present invention. Fats include esters of higher fatty acids, e.g., glycerides of $C_{10-24}$ fatty acids, alcohols, salts, ethers or mixtures thereof. They are classed among the lipids. It is also contemplated that emulsifiers to be included in conjunction with the fats. Emulsifiers include salts of ethanolamines with fatty acids and sulfated fats and oils. Preferred fats include compositions which have mono-,di- or tri-glyceryl esters of long chain of fatty acids. These include but are not limited to stearates, palmitates, laurates, linoleates, oleates, and residues or mixtures thereof having melting points greater than 50° C. U.S. Pat. No. 5,213,810 is directed to compositions including these materials and the '810 reference is hereby incorporated.

The coating process can be effected by spray coating with multiple fats or waxes onto the shearlite particles.

Such coatings can typically be used for taste-masking and controlled-release. As a result of the high uniformity and narrow size distribution, shearlite particles permit the use of substantially less coating materials to produce the intended effect. Thus, with a single complete but thin coat, a high degree of taste-masking and efficient controlled-release can be effected.

In order to illucidate this benefit, an example has been included hereinbelow (Example XII) wherein ibuprofen feedstock is coated and compared to ibuprofen shearlite particles which are coated. The two coated ibuprofen materials were compared for taste. The coated ibuprofen which was not converted to shearlite particles was unacceptable, whereas the processed ibuprofen (subsequently coated) was found to be highly acceptable. Microscopic examination of the unprocessed ibuprofen revealed agglomerated needles of ibuprofen which had varying thicknesses of coating. To the contrary, the shearlite ibuprofen particles displayed a uniform thickness of coating which is ideal for taste-masking and controlled-release.

Another manifestation of the present invention is the combination of a low melting coating such as a fat or wax with an active ingredient which has been transformed to shearlite particles. The material is extruded and sprayed using the flash shear process or traditional spray congealing.

In yet another example of the unique advantage provided by the present invention, an antidote material can be transformed to shearlite particles and then coated by an active ingredient. Both the antidote and the active ingredient may or may not include controlled-release agents to enhance dissolution or to retard dissolution. Any combination of active in antidote can be formulated depending on the need of the practitioner. Thus, the active agent can be the shearlite particle while the antidote can be the coating. Additional coatings can be included in a multiple coated product to provide active and antidote. Any combination of these agents suitable for the desired purpose are contemplated as covered by the present invention.

Furthermore, liquiflash processing and products from industrial chemicals which benefit from reduction in dusting and better flow properties are contemplated as part of the present invention. Such industrial chemicals include, but are not limited to, the following: phenol, styrene, butylated hydroxy anisole (BHA), tert butylhydroxy hydroquinone (TBHQ), hydroquinone, insecticides, herbicides, combinations of insecticides and herbicides, anti-fungals and other agents which suffer from dusting which may cause explosion or may endanger personnel by contact therewith.

BARRIER PROCESSING APPARATUS

Figure 3A:
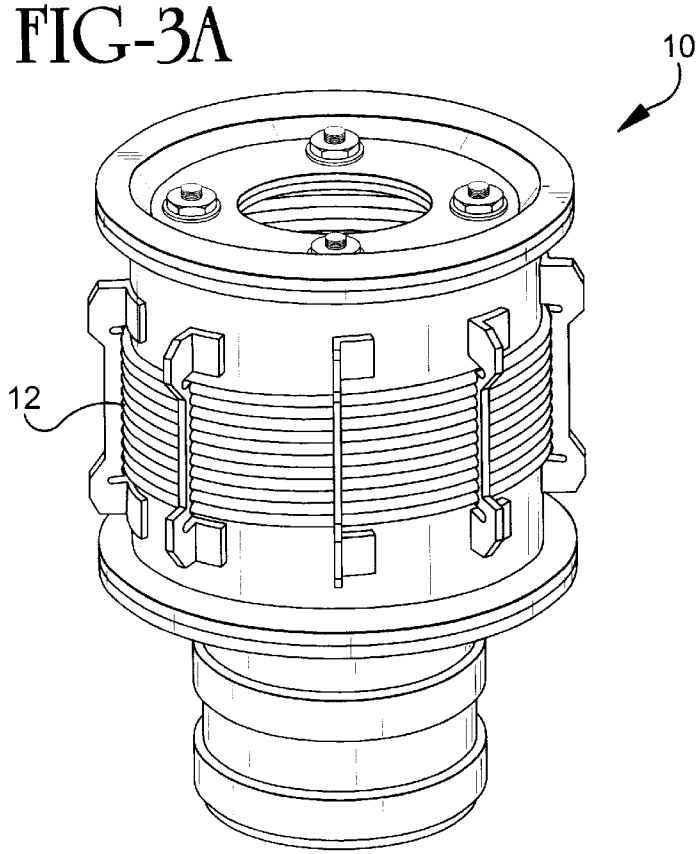
FIGS. 3A, 3B, and 3C depict one apparatus useful in the present invention.
Figure 3B:
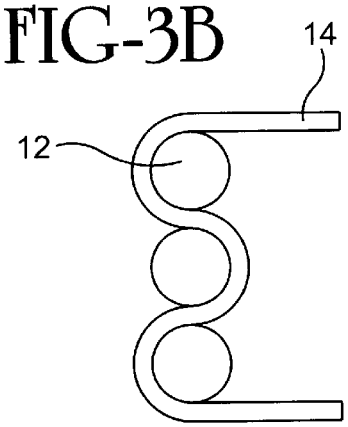
Figure 3C:
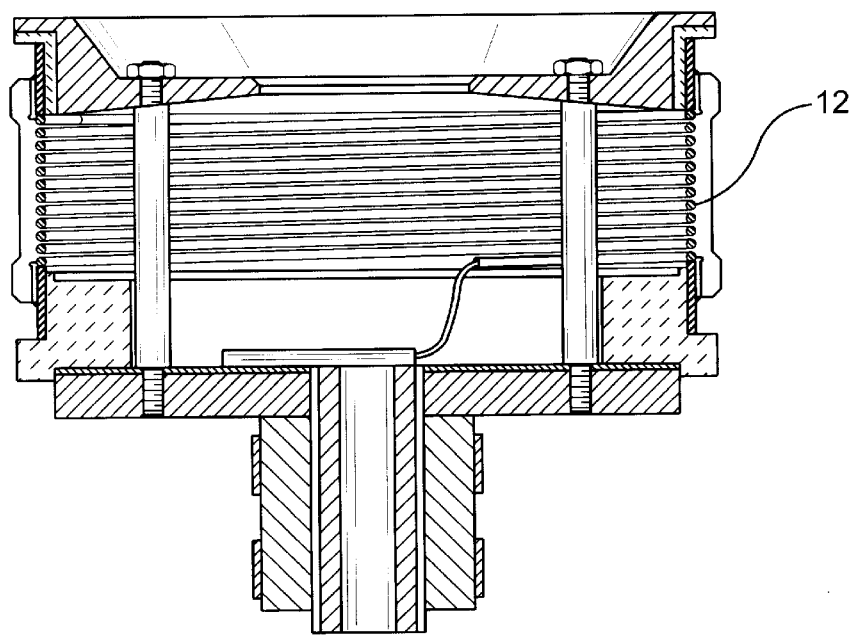

Referring to FIGS. 3A, 3B, and 3C, a first spinning head has been shown which can be used in the liquiflash process. The assembled head 10 is depicted in FIG. 3A. This head is of the type which is disclosed in U.S. Pat. No. 5,427,811 to Fuisz, et al. issued Jun. 27, 1995 and its continuation-in-part application bearing Ser. No. 08/192,133 filed Feb. 4, 1994, which is now U.S. Pat. No. 5,427,811 to Fuisz, et al. issued Jun. 27, 1995 (both of which are incorporated herein by reference).

Referring to the spinning head shown in FIG. 3A, a heating element(s) are depicted as continuous cable 12 which is helically wound thereabout. The cable heating element can consist of several cables or even just one cable which is continuously wound around the periphery of the head 10. The embodiments disclosed in the two (2) applications referred to above have certain characteristics, such as slits, etc., for flash flow processing.

In the present invention, however, the small openings in the head are achieved by lacing a shim 14 between the coils of the heater 10. FIG. 3C is a diagrammatic sketch of this embodiment. The shim material 14 is preferably a very thin strip of food grade metal such as stainless steel. The thickness of the shim can be from 0.001 to 0.006 inch in thickness. Preferably, the thickness of the shim is about 0.002 inch. The shim can be about 0.100 inches wide. The lacing can be provided at several locations around the perimeter of the head. Furthermore, teflon coating insulators can be provided in conjunction with the heating cable in order to reduce the friction of the surface of the heating elements.

Figure 4A:
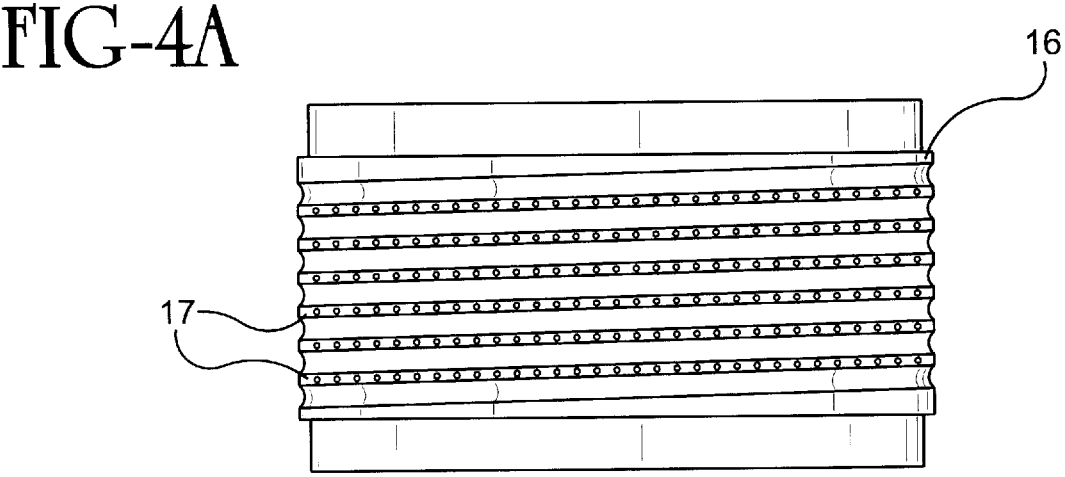
FIGS. 4A, 4B, and 4C depict a second apparatus which has been used in the present invention.
Figure 4B:
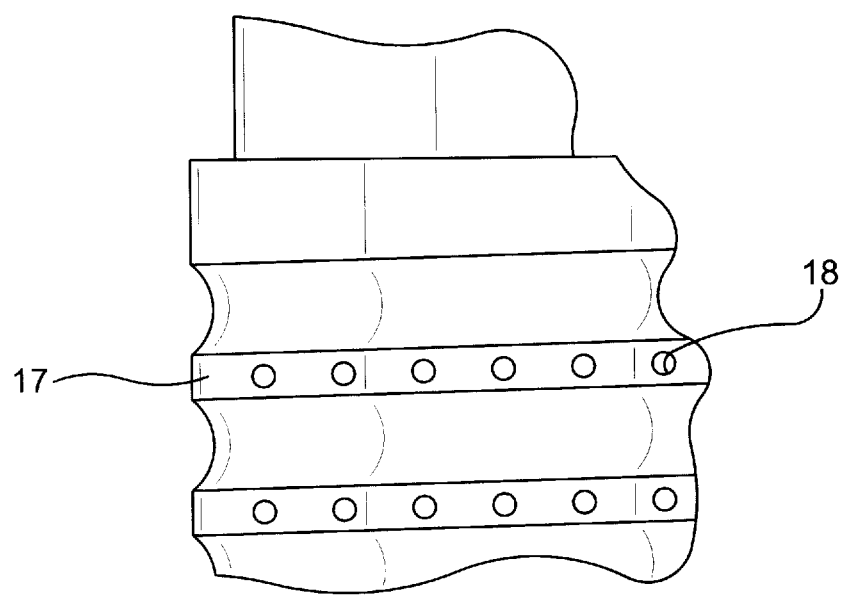
Figure 4C:
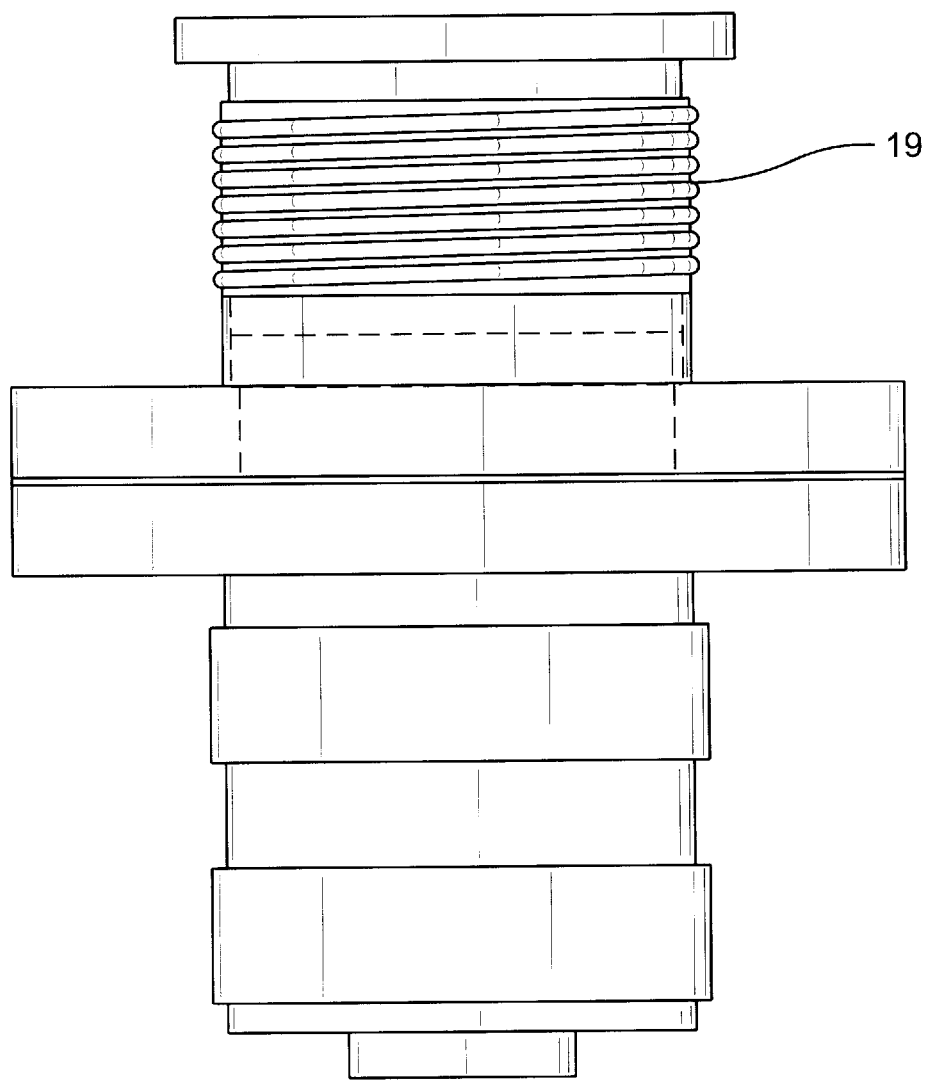

Yet another embodiment of apparatus which can be used in the present invention is shown in FIGS. 4A, 4B, and 4C. The apparatus of the type used herein has been disclosed in U.S. application Ser. No. 08/226,234 filed Jun. 27, 1994, now U.S. Pat. No. 5,445,769 to Rutkowski, et al. issued Aug. 29, 1995 (which is incorporated herein by reference).

Referring to FIGS. 4A–C, a spinning head silhouette 16 is shown having spaced apart protruding ribs 17 in which tiny openings have been drilled. Preferably the openings are on the order of 0.020 inches in diameter. Referring to FIG. 4B, a cut-away section of the head of FIG. 4A is shown with the holes 18 in the raised ribs 17. A heating element 19 can then be wound around the outside surface of the head 16 in order to provide heat sufficient to melt the feedstock on the interior surface of the spinning head.

The spacing and configuration of the holes can be adjusted by those skilled in the art to achieve the results which are desired. A discussion of this has been fully set forth in the above-identified pending U.S. application. Other variations of this embodiment including size of holes, spacing between the holes, and shape of the openings through the head can be varied depending upon the application. It has also been found that the openings in the configuration shown in FIGS. 4A–C are ideally provided by drilling with a laser beam.

Figure 5A:
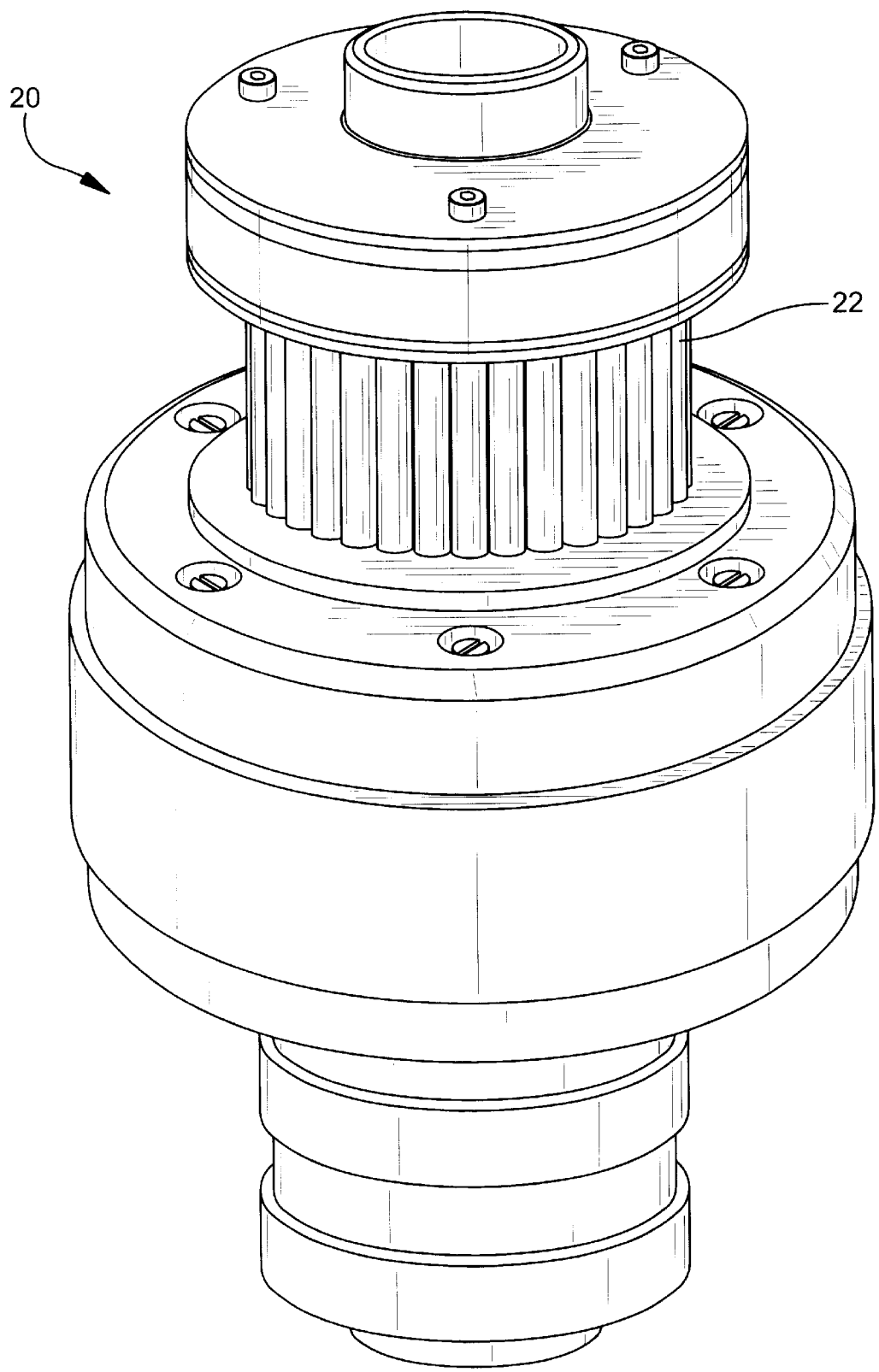
FIGS. 5A, 5B, and 5C depict a third apparatus used in the process of the present invention.
Figure 5B:
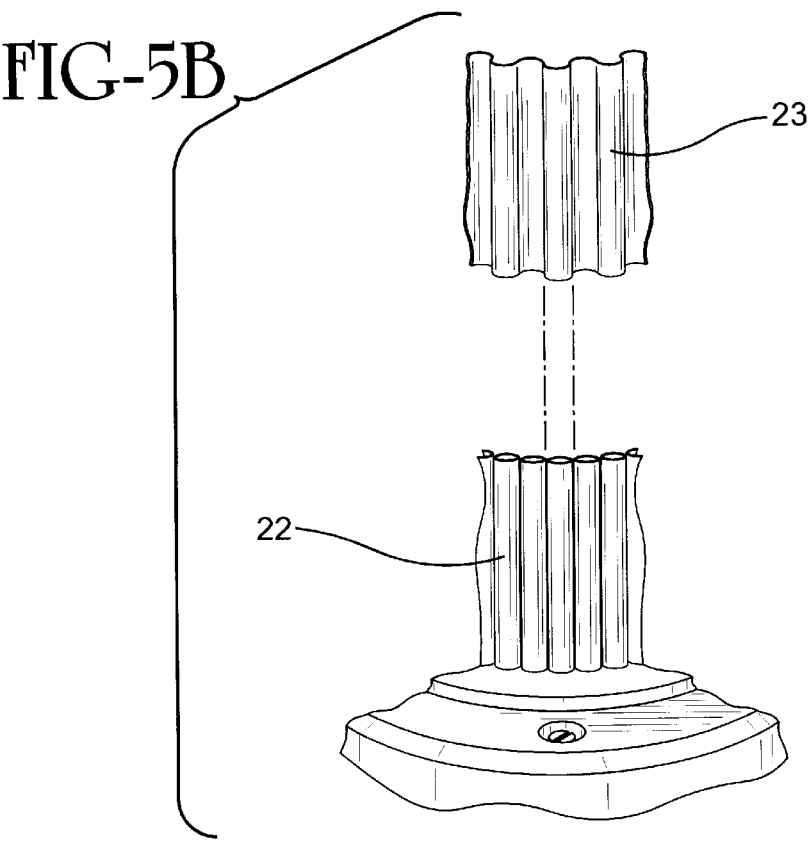
Figure 5C:
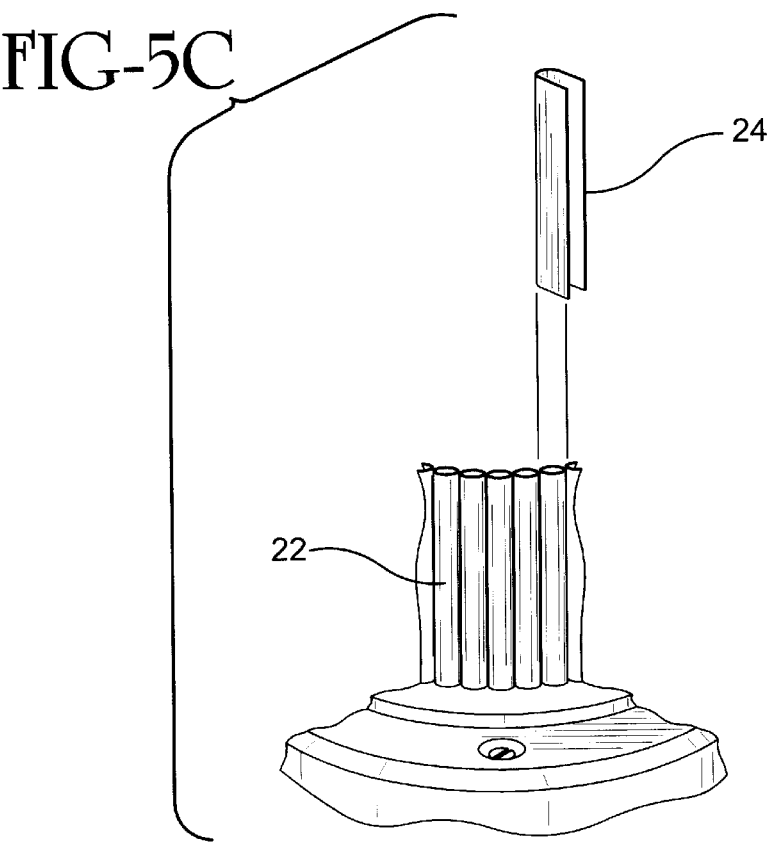

Yet another apparatus used in the present process is shown in FIGS. 5A, 5B, and 5C. The apparatus shown in these figures is of the type disclosed in commonly owned copending U.S. application bearing U.S. application Ser. No. 08/330,938 filed Oct. 28, 1994, now U.S. Pat. No. 5,458,823 to Perkins, et al. issued Oct. 17, 1995. In FIG. 5A, a spinning head 20 is shown with upright closely spaced heating elements 22. In a preferred embodiment, electrical current can be provided to each element. In this way, a high degree of control can be maintained over the heat supplied to the processing barrier. Furthermore, the elements can be spaced as closely together as possible in order to provide a restricted passageway for passage of liquiform material.

Figure 2A:
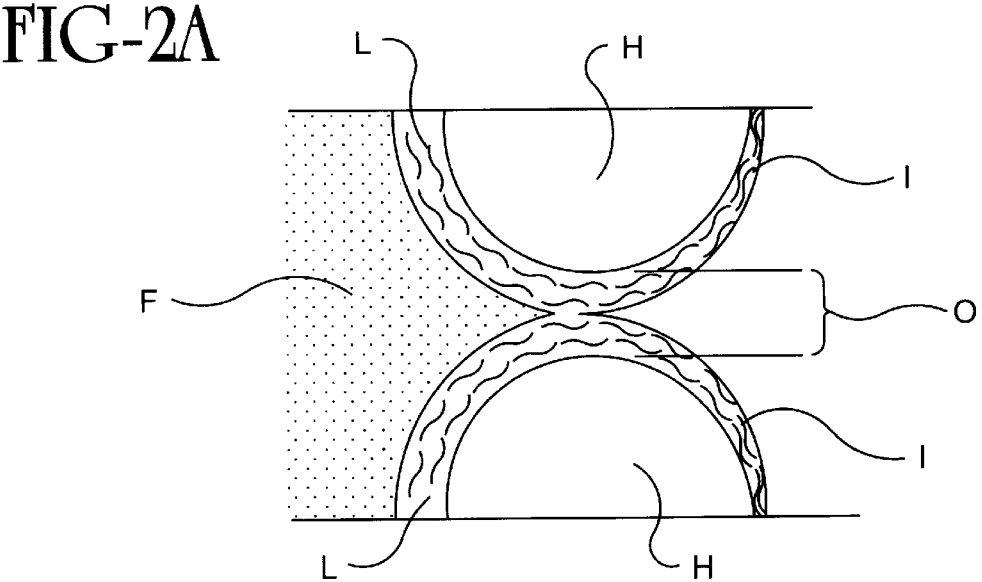
FIGS. 2A, 2B, and 2C are schematic representations of the liquiflash process in accordance with the present invention.
Figure 2B:
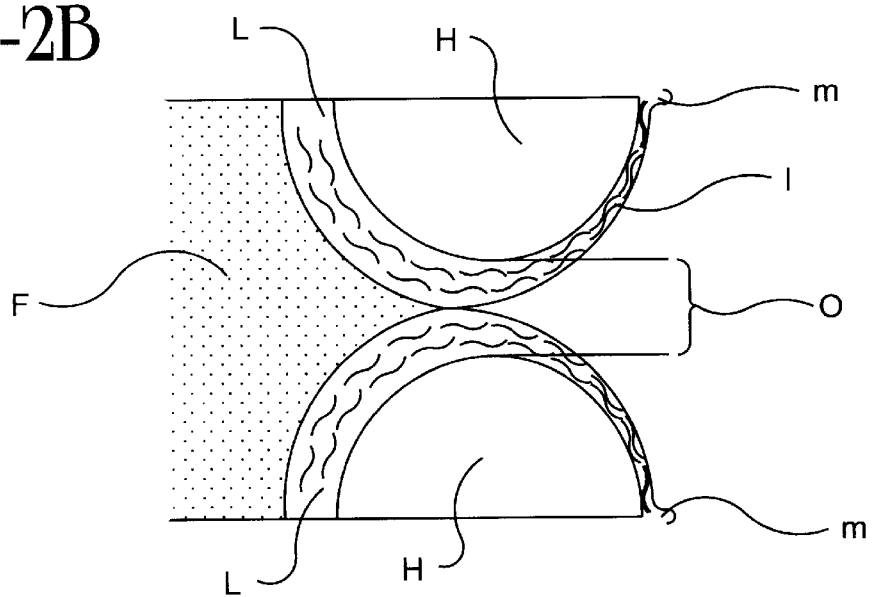
Figure 2C:
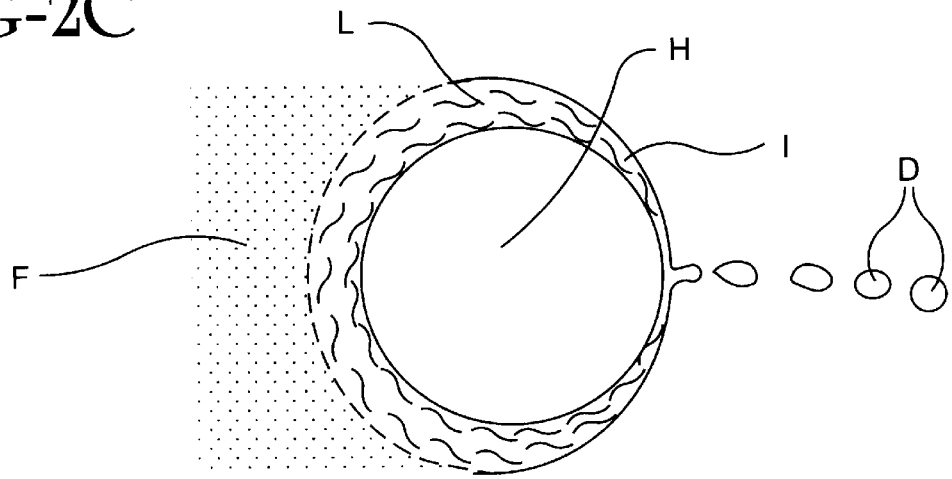

In another preferred embodiment as shown in FIG. 2B, a continuous screen can be interwoven between the heating elements in order to affect the size of openings through the barrier and also to provide a barrier with relief which enhances drop formation. It has been found that screens with 60 mesh and 30 mesh can be used. The actual opening size, e.g., mesh, can be selected by the artisan.

In yet another embodiment, each heating element 22 can be individually provided with a shim 24 which further reduce the size between the heating elements. As a result of using the shims, opening sizes on the order of 0.005–0.007 inch can be reduced to openings on the order of 0.002 inch.

In each of the embodiments, the head has a diameter of about 3 inches. The apparatus in the present invention has currently been run at a rotational velocity in the area from around 3,000–5,000 rpm. The actual speed can vary from as low as 500 rpm to as great as 100,000 rpm. It is contemplated that many commercial embodiments will be run in the area of 35,000–40,000 rpm. Once again, the size of the head and the rotational speed of the head will depend on the desired results, and other factors such as the size and nature of the feedstock, and the ambient atmosphere adjacent to the spinning head.

Figure 6B:
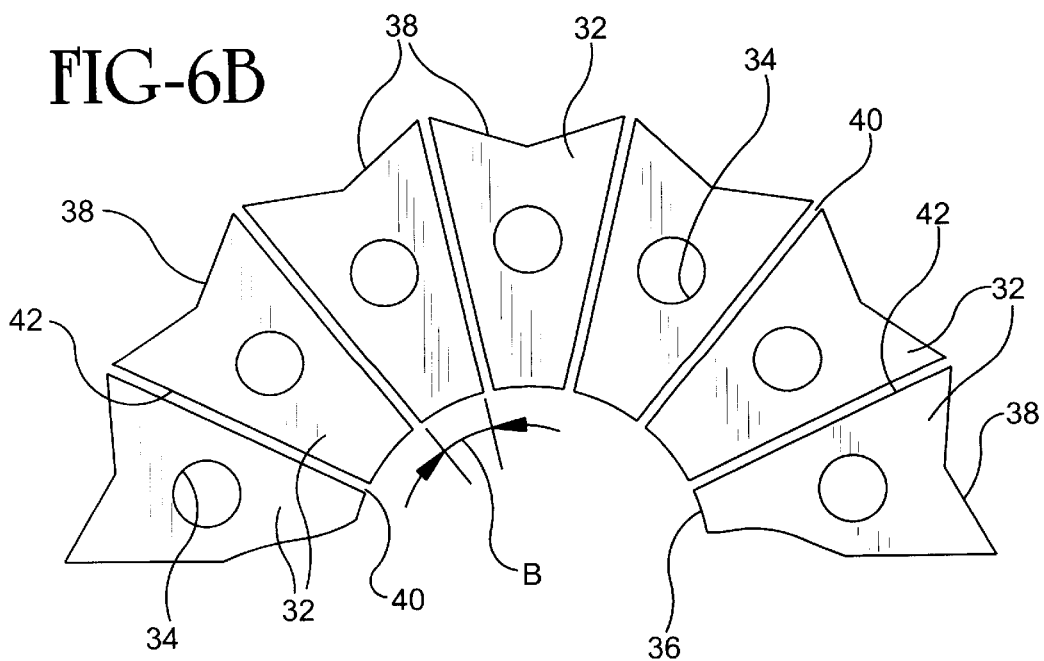

Referring to FIGS. 6A and 6B, a further modification of spinner head 10, particular useful with pharmaceutical product, as described above, is shown. Spinner head 10 is modified in a manner similar to the embodiment set forth above wherein a number of tubular heating elements 30 have been provided. However, in order to narrow the opening through which feedstock materials expelled, this embodiment employs individual modular blocks 32 which fit over heating elements 30.

Each modular block 32 includes a metallic heat conductive body having a central cylindrical passage 34 therethrough which is constructed and arranged to accommodate individual tubular heating elements 30. Each modular block 30 also has a generally trapezoidal cross-section having a smaller wall 36 which faces inwardly toward the feedstock chamber and an opposite wider outer wall 38. In a preferred form, the outer wall 38 may include angular surface 39, which provides for longer opposed side walls 40 and 42 without increasing the mass of modular blocks 30. The modular blocks 30 can be slipped over tubular heating elements 30. As shown in FIG. 6B, walls 40 and 42 form radially directed slots between adjacent modular blocks 32 through which feedstock material may be processed and expelled in a manner similar to that explained above with respect to the previous embodiments. The radially directed slots can be adjusted to alter the size of the passage through which the feedstock material is expelled.

As shown in FIG. 6B, blocks 32 can be rotated about tubular heating element 30 (see arrows B) to cant or twist the blocks, thereby changing the spacing and/or direction of the slots. The rotation of blocks 32 can be accomplished individually or may be rotated in unison with an appropriate mechanism (not shown). With such a mechanism, modular blocks 32 may move in a manner similar to an iris diaphragm of a camera to increase or decrease the size of the passage defined by the slots.

Figure 7:
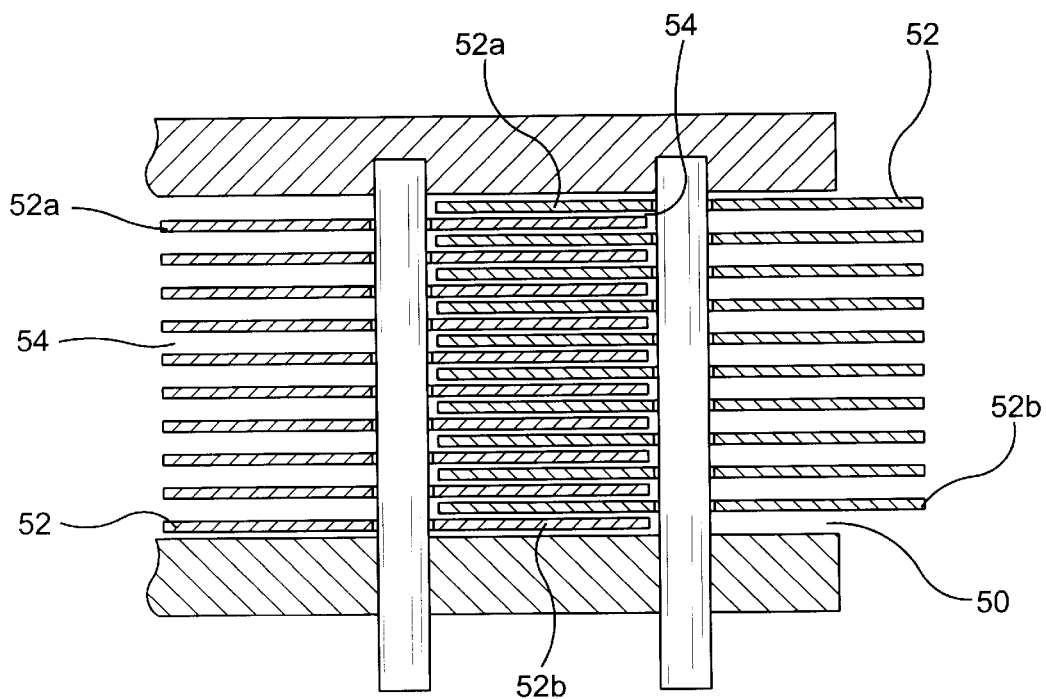
FIG. 7 depicts an additional apparatus used in the present invention.

A further construction of block 50 is shown in FIG. 7, where transverse slots are formed. Modular block 50 can include a body formed to have a series of vertically spaced horizontally extending fins 52. Modular block 50 can be constructed so that one set of fins 52a interleave with an adjacent set of fins 52b of an adjacent modular block 50. In this manner a series of vertically spaced transverse slots 54 are formed through which feedstock material may be processed.

Figure 8:
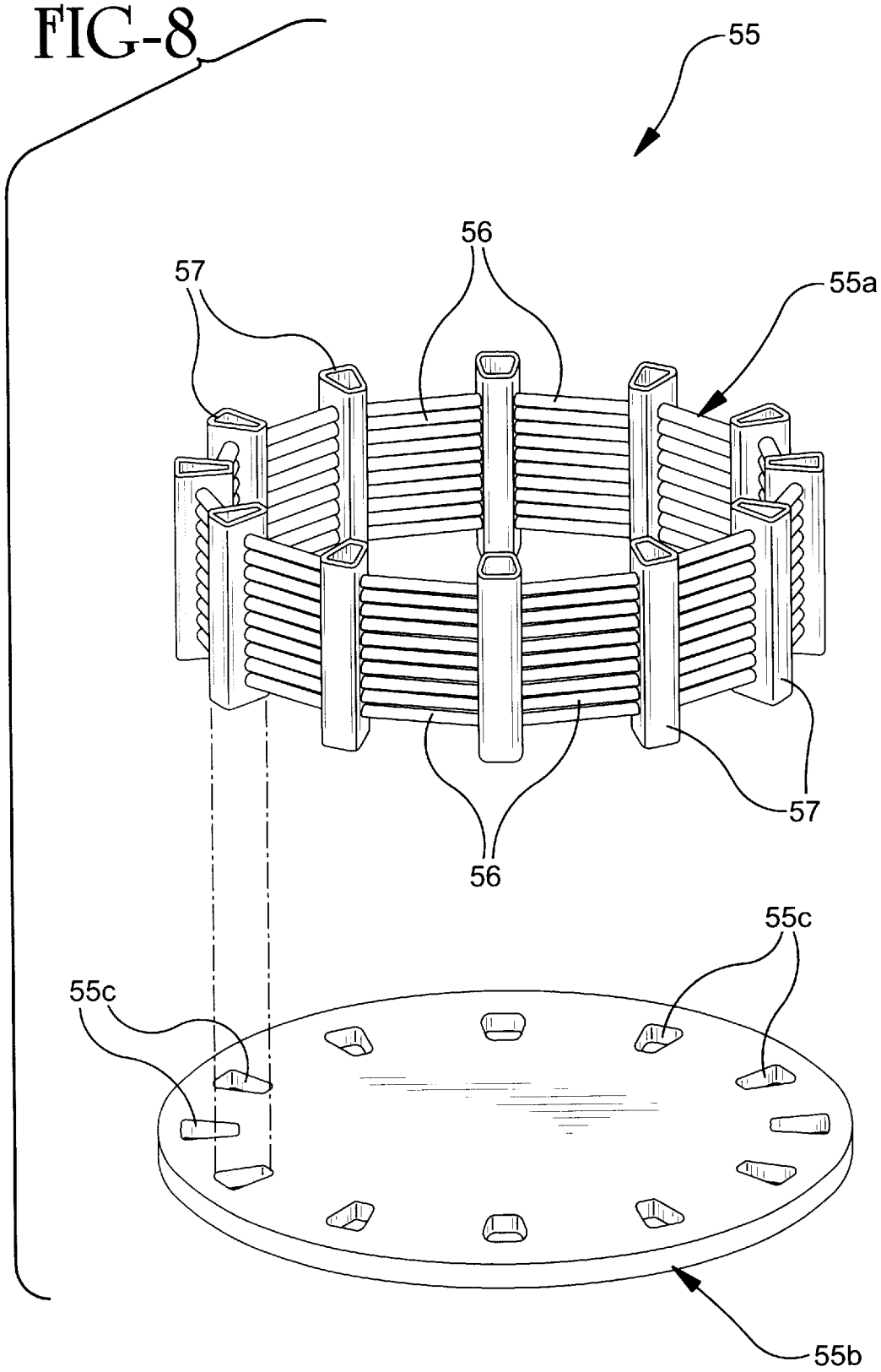
FIG. 8 depicts another apparatus used in the present invention.

Referring now to FIG. 8, still further embodiment of the spinner head of the present invention is shown. Spinner head 55 of the present invention includes a generally circumferential array 55a of horizontally disposed tubular heating elements 56. A set of vertically spaced horizontally extending heating elements 56 can be positioned between an adjacent pair of vertically extending support elements 57. Each of support elements 57 can be positioned and spaced in circumferential fashion about base 55b. Appropriately, configured retaining openings 55c are provided to accommodate support elements 57.

Horizontally disposed tubular heating elements 56 can be of similar construction to tubular elements previously described hereinabove. All or selected ones of tubular heating elements 56 may be individually powered in accordance with the present invention. It is also contemplated that vertical support elements 57 in additional to supporting horizontally extending tubular heating elements 56 may also provide a common power bus to energize the individual tubular heating elements. Vertical support elements 57 include appropriate openings spaced therealong which accommodate the ends of tubular heating elements 56 therein in an interference fit such that the securement between the tubular heating elements 56 and the vertical support elements 57 is achieved under both ambient and running temperatures. The space is between adjacent horizontally disposed tubular heating elements 56 can be adjusted to vary the openings through which feedstock material is processed.

It is further contemplated that tubular heating elements of uniform size and configuration or of differing size and configuration may be employed within the same spinner head. An arrangement of the same or different size tubular heating elements allows the spinner head to be statically and/or diametrically balanced. As described above with respect to the spinner head having vertically disposed tubular heating elements, horizontally positioned tubular heating elements 56 of the present embodiment can be canted are skewed with respect to support elements 57.

Furthermore, even though FIG. 8 shows one circumferential arrangement of array 55a, other arrangements are also within the contemplation of the present invention. Further, plural concentric sets of arrays of horizontally disposed tubular heating elements are within the contemplation of the present invention.

The embodiment shown in FIG. 8 also has particular utility with respect to pharmaceutical products since the individual tubular heating elements 56 supported between a common bus such as vertical support element 57 can be easily removed for cleaning as necessary in the processing of pharmaceutical products.

Those skilled in the art will appreciate that other factors will directly affect the size and shape of the apparatus, and is intended to include all variations that come within the spirit of the invention as defined in the appended claims.

EXAMPLES

Example I

Sucrose Spheres

In the first example, the apparatus disclosed in FIG. 5A was used in the liquiflash process for transforming sucrose. The opening between adjacent heating elements in the apparatus shown in FIG. 5A was 0.20 inches. The head was spun at 3600 rpm as it was heated to 180° C.

As the temperature reached its peak, sucrose was subjected to liquiflash conditions and exited the spinning head as a result of centrifugal force. Solid spheres were formed which ranged in size from about 100–200 $\mu$m in diameter. The very unique and uniform size distribution is clearly shown in the photomicrograph herein at FIG. 9. The magnification of FIG. 6 is 50.

Figure 9:
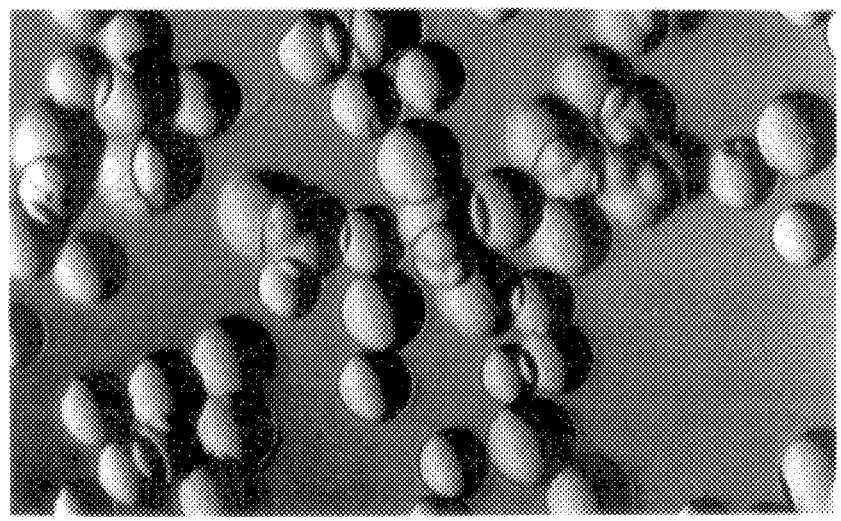
FIG. 9 is a photomicrograph of a sucrose product prepared in accordance with the present invention.

In this particular case, the size of the rock candy prevented passage through the barrier and provided delay at the barrier sufficient to cause sucrose to transform to liquiform and be instantaneously processed to the highly uniform microspheres depicted in FIG. 9. These spheres are substantially solid throughout, and can be used in a variety of ways, such as a substrate for depositing of material thereon.

It should be noted that microspheres having a diameter of from about 5–50 μm and preferably around 25 μm are excellent for use in conjunction with chocolate. Very small and highly uniform microspheres enable the practitioner to provide a highly acceptable low fat chocolate product. Thus, the processing of sucrose, such as in the form of rock sugar, could be used quite effectively to provide an ingredient for the preparation of a chocolate product.

Example II

Acetaminophen Spheres

In this example, acetaminophen was processed using the apparatus showed in FIG. 5B wherein the screen was a 60 mesh screen positioned in serpentine fashion between adjacent heating elements. Acetaminophen powder (melting point 169°–170.5° C.) was fed to a spinning head run at about 3600 rpm. While the feedstock was subjected to centrifugal force, the temperature was raised until the acetaminophen powder was reduced to liquiform. The force generated by the spinning head expelled acetaminophen out of the spinner head, and impelled it through the 60 mesh screen. The product was permitted to free fall below the head a distance of from about 6 to 8 feet.

During this transition, fine spheres all of which were less than about 420 μm, were formed. 4.33 kilograms of this material was passed through a 40 mesh screen and 1.39 kilogram of the product was retained.

Figure 1B:
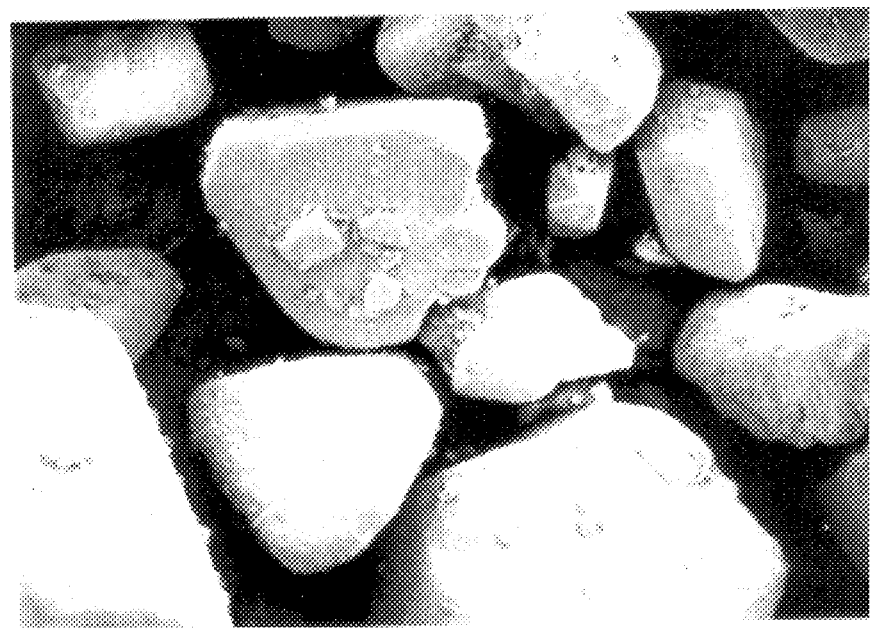
Figure 1C:
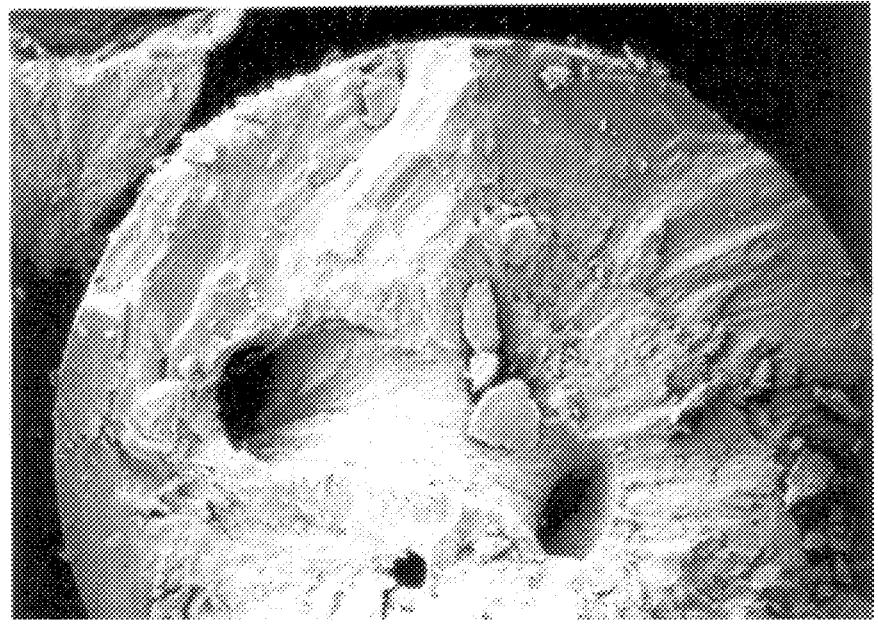

The feedstock, and product resulting from this experiment have been shown herein in FIGS. 1A, 1B, and 1C. In FIG. 1B, a photomicrograph of the feedstock is shown at 125 magnification. After processing, the resulting product was collected and a photomicrograph taken which is shown in FIG. 1A. As can be seen, a highly consistent and very uniform spherical product was produced. Comparing the product shown in FIG. 1A to the feedstock at FIG. 1B, the skilled artisan can readily ascertain the enhanced predictability and processability which is provided as a result of the present invention. FIG. 1C is a photomicrograph at 500 magnification taken of a cross section of a sphere shown in FIG. 1A. As can be seen, the sphere is substantially solid throughout having virtually no openings or voids therein. Once again, this product enables the artisan to provide a highly efficient drug product which can be used readily in delivery systems.

Example III

Coated Acetaminophen Spheres

Acetaminophen spheres prepared in Example II, were then coated with a formula consisting of 2.5 Eudragit® E100, 7.5% ethocel in a solvent having acetone and methanol in 5 to 1 ratio. Eudragit® is a polymer of methacrylic acid and methyl methacrylate available from Rohm Pharmo, Wetterstadt, Germany.

Figure 10:
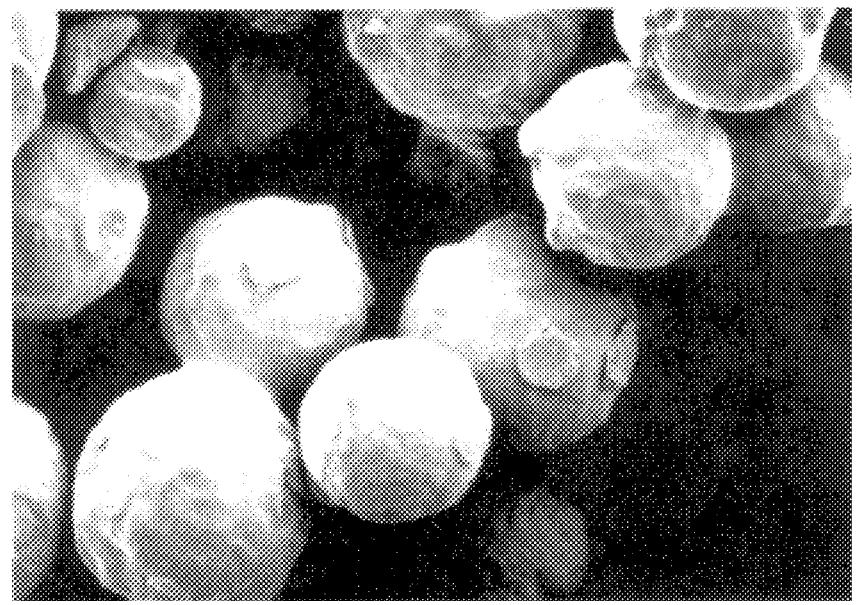
FIG. 10 is a photomicrograph of another embodiment of the present invention wherein microspheres produced in accordance with Example II have been coated.

The finished product provided 568 grams of finely coated acetaminophen beads. The coated product of the present example has been shown herein in FIG. 10 at 125 magnification. A very uniform coated product has been shown which can be easily used in feeding the coated active ingredient to machinery for tabletting and for the purpose of filling capsules.

Thin, uniform coatings such as that provided herein results in much less coating material required to obtain better resulting taste masking and controlled release. As a result of the monodispersed characteristic of the present product, there is less loss of product as a result of oversize material.

Coating in general is tremendously enhanced by providing a uniformly dispersed microsphere of the present invention. For example, in fluidized-bed type coating, the equilibrium condition established in the fluidized bed has a tendency to retain particles having a similar size for consistent and efficient coating. Thus, large and small particles outside the range of the uniform particle size leave the bed during coating. In that case, the active ingredient must be recycled and reprocessed to obtain the active ingredient for coating. In the present invention, non-uniform sizes are virtually eliminated.

Example IV

Ibuprofen Spheres

Using the same apparatus as shown in FIG. 5B, with a 60 mesh screen, ibuprofen was processed in accordance with the present invention.

An ibuprofen powder feedstock was fed to the spinning head and the head was rotated at about 4800 rpm while the heating elements were raised to a temperature which produced the liquiflash conditions. The feedstock also consisted of 15% Compritol 888 ATO and 5% Gelucire 50/13. (Compritol 888 ATO is a glycerol behenate NF made available by Gattefosse S.A., a French company. Gelucire is surfactant also available from Gattefosse S.A.).

Figure 11:
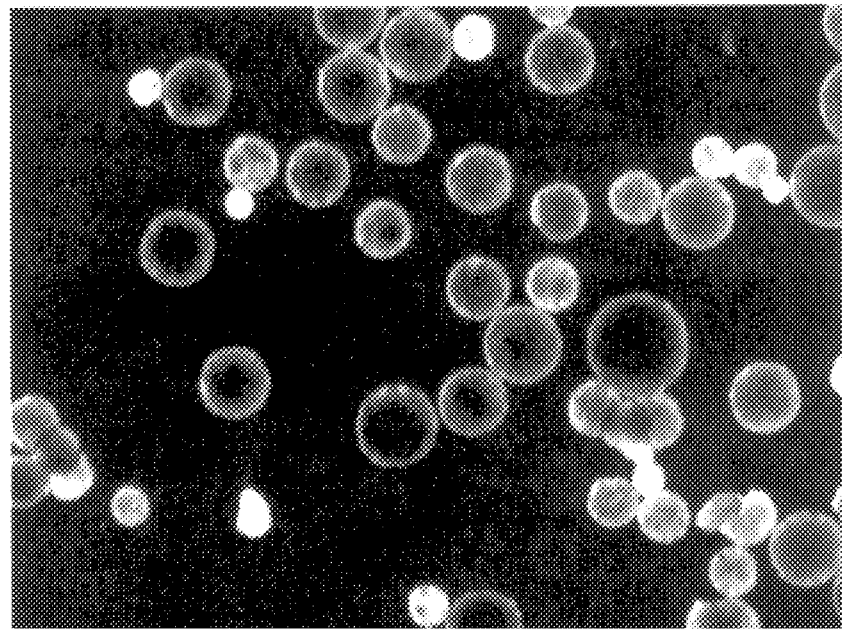
FIG. 11 is a photomicrograph of ibuprofen shearlite product prepared in accordance with the present invention.

The spinning head forced the material through the screen and the product was permitted to free fall a distance of from 6–8 feet below the spinning head. The product collected is shown in the photomicrograph of FIG. 11 which has a magnification of 50. As can be seen from FIG. 11, the spheres have a highly consistent particle size ranging from about 50–200 microns in diameter.

Figure 11A:
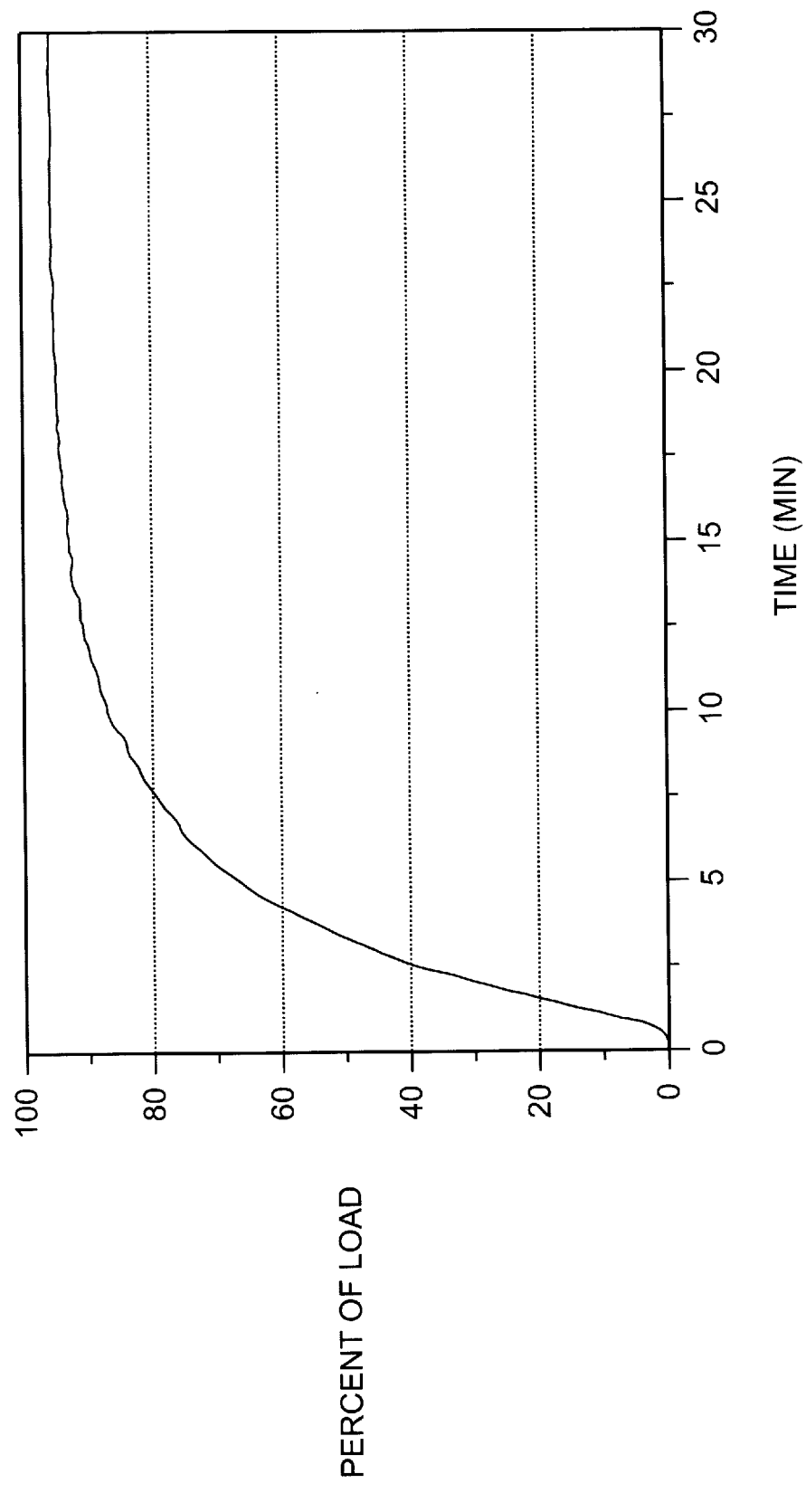
FIG. 11A is a graph which depicts dissolution of ibuprofen shown in FIG. 11.

The product was also subjected to dissolution testing to determine the time required for dissolution of the active ingredient. The monograph is provided by the U.S. Pharmacopoeial Convention, Inc. in the U.S. Pharmacopoeial National Formulary Monograph For Ibuprofen Dissolution Study, U.S. 23 NF 18, page 786 (1995). The results have been shown in FIG. 11A. At a composition level of 80% ibuprofen, it can be seen that the time for dissolution of most of the ibuprofen occurred at about 15 minutes and virtually total dissolution occurred at around 20–25 minutes. These results show high predictability for delivery to a bio-system by use of microspheres produced in accordance with the present invention.

Example V

Ascorbic Acid Spheres

In this Example, ascorbic acid was processed by the liquiflash process using the apparatus described in FIG. 5C. As a result of the short brass veins having a thickness of about 0.006 inches surrounding each of the heating elements, gaps of 0.002 inches were provided. Moreover, the head was positioned 10 feet from the collecting surface to permit an unobstructed formation and solidification of shearlite particles in accordance with the present invention.

Ascorbic acid powder was fed into the spinner revolving at about 1800 rpm while the head was heated to a point at which the powder was changed to liquiform for purposes of liquiflash processing. Fine beads were expelled from the is spinning head. Bead formation began after about 15 seconds and the product formation was completed in about 15–20 seconds actual spinning time.

The bead size production was as follows:
0.10% retained on No. 10 mesh, 0.62% on No. 20 mesh, 21.10% on No. 40 mesh, 40.35% on No. 60 mesh, 23.10% on No. 80 mesh, and 14.70% passed through No. 80 mesh. Thus, it can be seen that a high degree of predictability of shearlites were produced from ascorbic acid using the process of the present invention.

Example VI

Ascorbic Acid Tablet Production Without A Binder

The ascorbic acids shearlite particles produced in accordance with Example IV were classified according sieve size. The portion passing through the No. 80 mesh was used to feed a tabletting press. The tabletting press used was a Specac Model 15.011 tablet press.

Quite interestingly, the ascorbic acid product was able to be fed efficiently into the tablet press using a very small angle of repose. By angle of repose, it is meant the angle required to induce flow of the tablet feedstock into the tablet press. A low angle of repose is highly desirable for purpose of efficient processing.

Tablets were produced under 42 tons per square inch of pressure. The resulting tablets displayed excellent cohesiveness and have a shiny surface which exhibited no sticking during removal from the die. Moreover, the superior tablet product prepared as a result of the present invention did not require a binder or any other additive to ensure cohesiveness of the tablet.

Example VII

Pseudoephedrine Beads

Two experiments were run to determine the processability of pseudoephedrine as a feedstock material. The apparatus used in these examples is that depicted and described in FIGS. 4A, 4B, and 4C.

A feedstock consisting of 95% pseudoephedrine (Kroll 331151) and 5% polyethylene glycol (PEG 1450) was prepared by melting the polyethylene glycol and adding thereto the pseudoephedrine and blending and then permitting the mixtures to solidify. The solidified mixture was then powdered in a grinding apparatus.

The spinning head was spun at 3300 rpm and the feedstock material was introduced until the material was reduced to liquiflash condition. The product resulting therefrom was very uniform in shape and the majority of the spheres were around 160 microns.

Figure 12A:
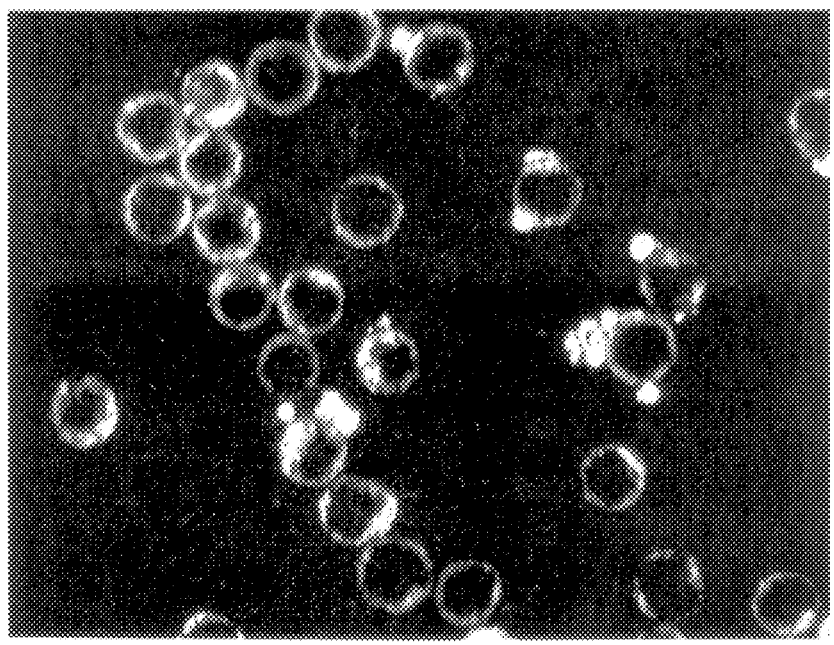
FIGS. 12A and 12B are photomicrographs of pseudoephedrine prepared in accordance with the present invention.

The results of this first experiment are shown in the photomicrograph of FIG. 12A, and the dissolution characteristics have been depicted in 12C and 12D. As can be seen from these figures, the product was a very uniform spherical bead which demonstrated immediate dissolution of the active ingredient. The actual content of pseudoephedrine in the product shown in FIGS. 12A and 12B was 95%.

A second portion of this example was performed using the same ingredients as reported in the first experiment and the outcome was also similar.

Figure 12B:
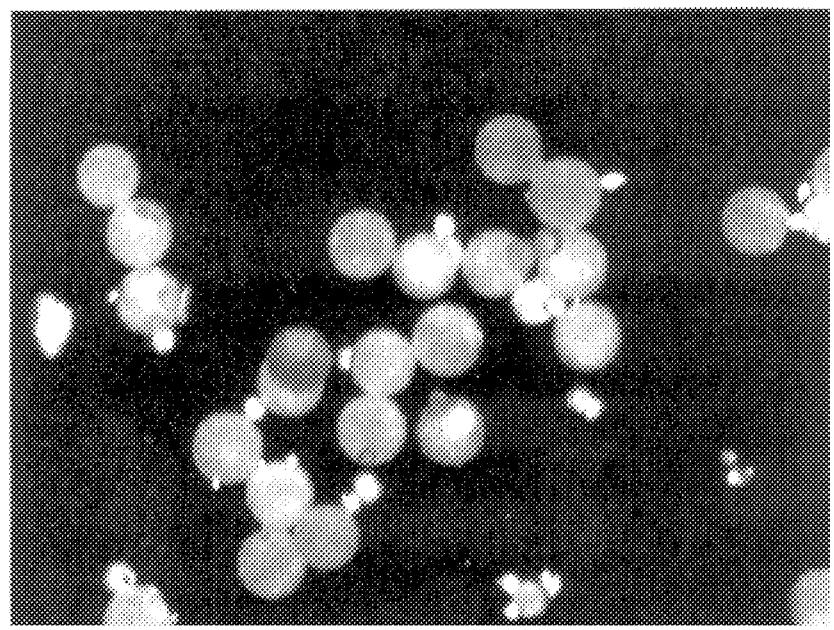
Figure 12C:
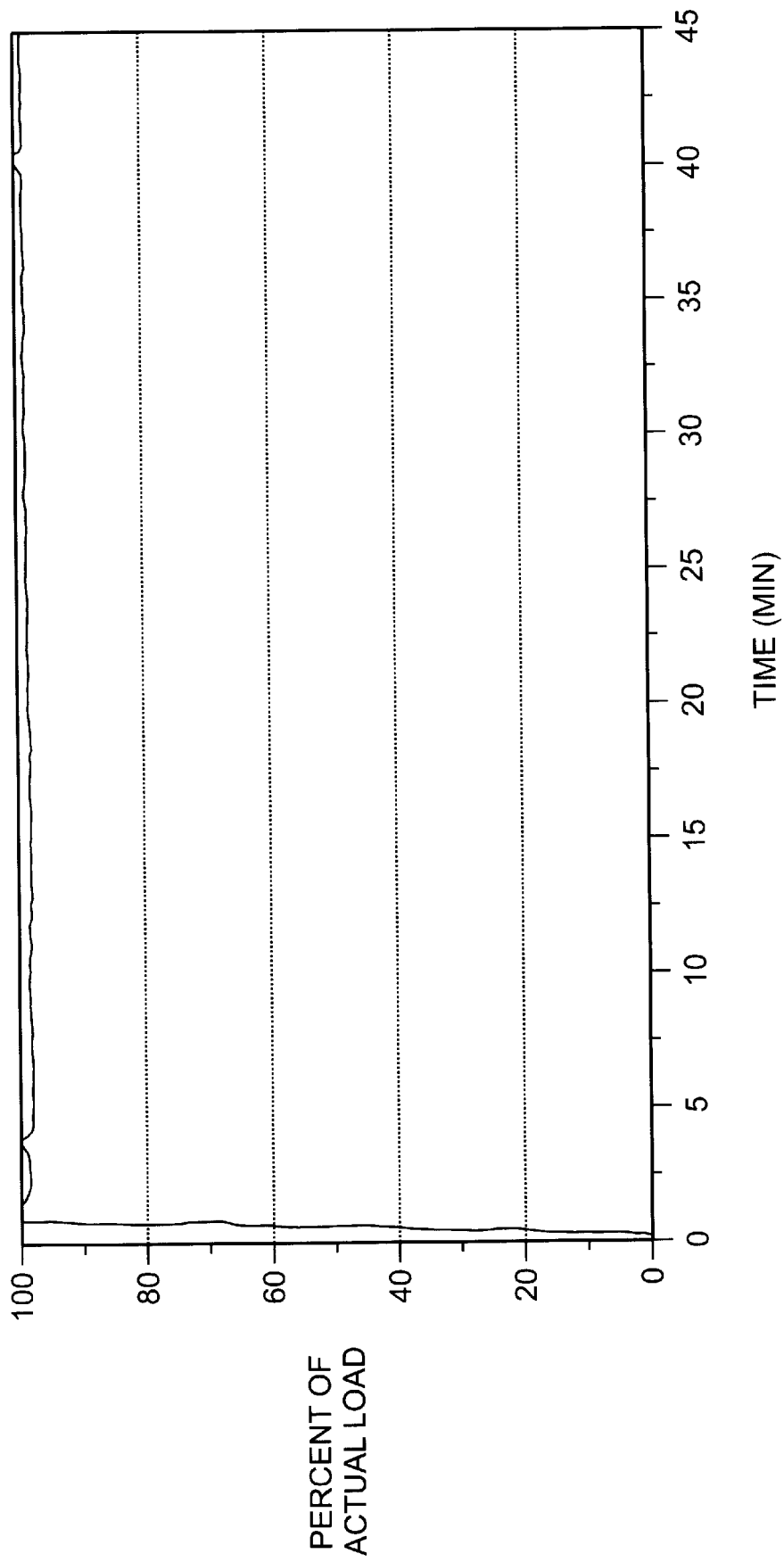
FIGS. 12C and 12D are graphs which depict the dissolution of the products shown in FIGS. 12A and 12B, respectively.
Figure 12D:
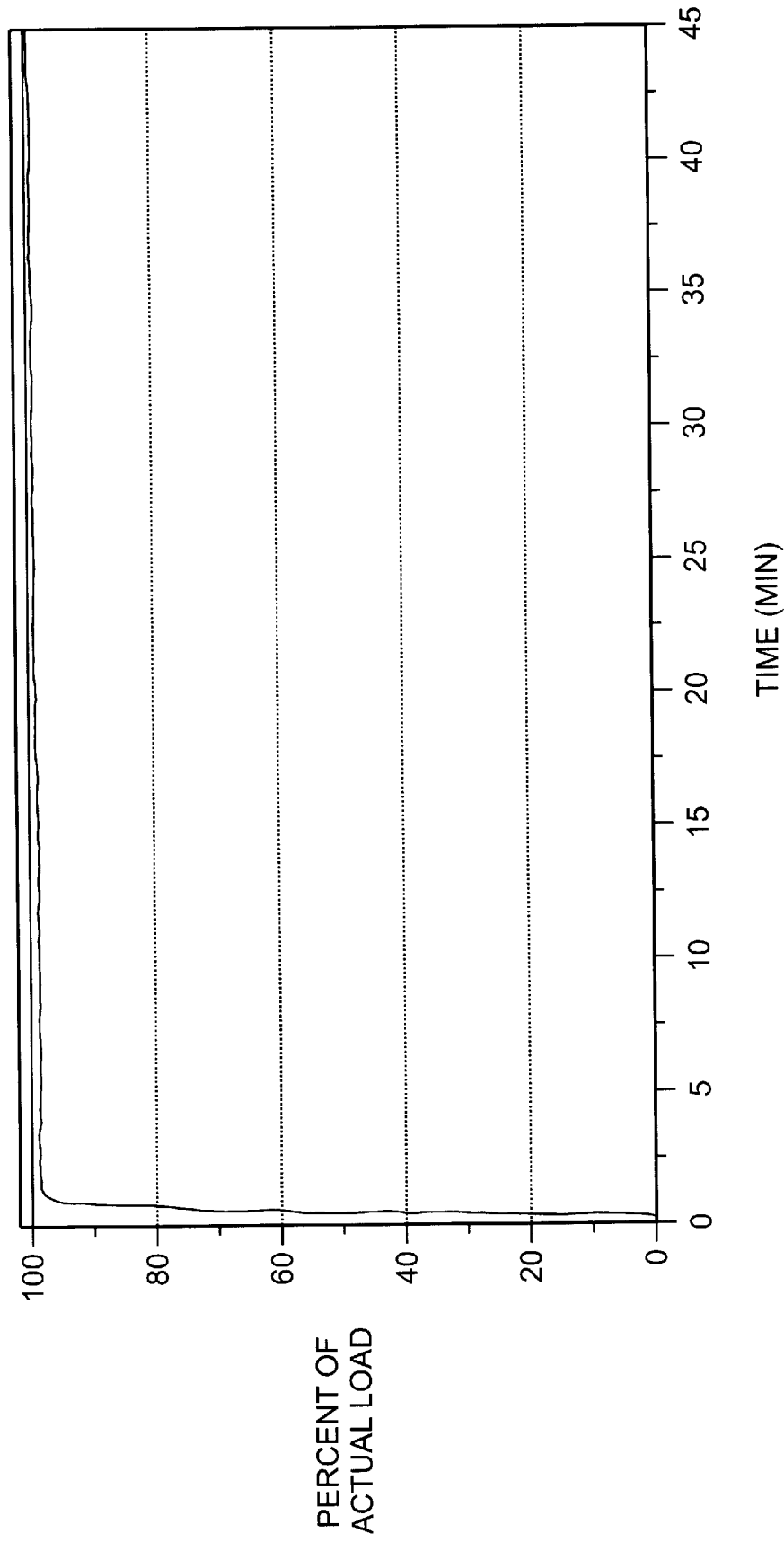

The product, which has been shown here in FIG. 12B has a very uniform spherical shape having a size of between 160 and 180 μm. The actual content of active ingredient was 96.06%. The dissolution characteristics are shown in FIGS. 12C and 12D which depicts an excellent and predictable release rate of the active ingredient.

Example VIII

Pseudoephedrine And Glycerol Monostearate

In this example, 30% pseudoephedrine and 70% glycerol monostearate (Myverol 18-06) was blended and introduced to the apparatus shown in FIGS. 4A, 4B, and 4C. The head was spun at 3300 rpm and the temperature raised until the feedstock became liquiform.

Figure 13:
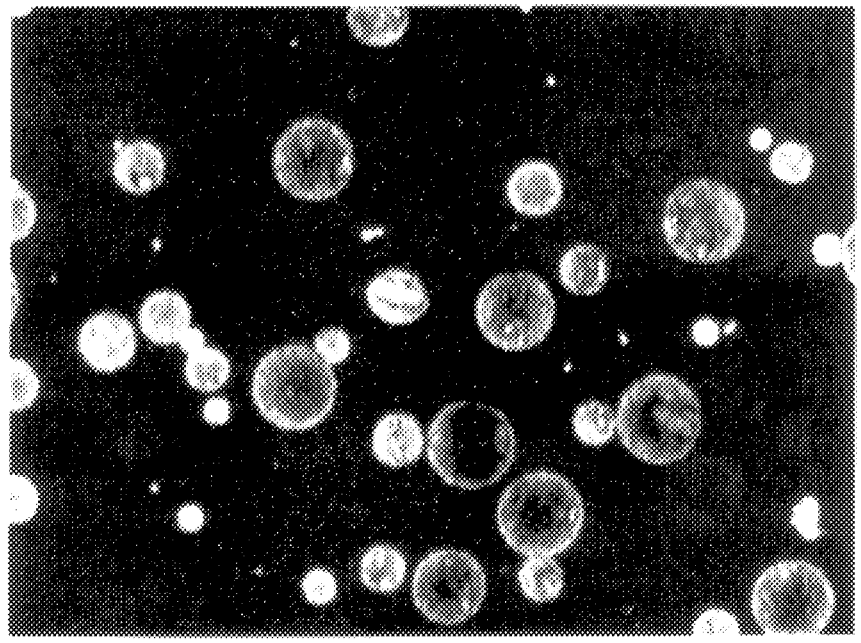
FIG. 13 is a photomicrograph which depicts a pseudoephedrine product prepared in accordance with the invention.

The product formed as a result of the liquiflash processing was a uniform spherical product ideally suited for inclusion in a delivery system. The product is shown in FIG. 13, which is a photomicrograph taken at 50 magnification.

Example IX

Dextromethorphan and Glycerol Monostearate

In this example, the active, dextromethorphan, was mixed with glycerol monostearate (Myverol 18-06). Dextromethorphan HBr (30%) was mixed with 70% Myverol 18-06 brand glycerol monostearate blended and then introduced to a spinning head as described above.

Figure 14:
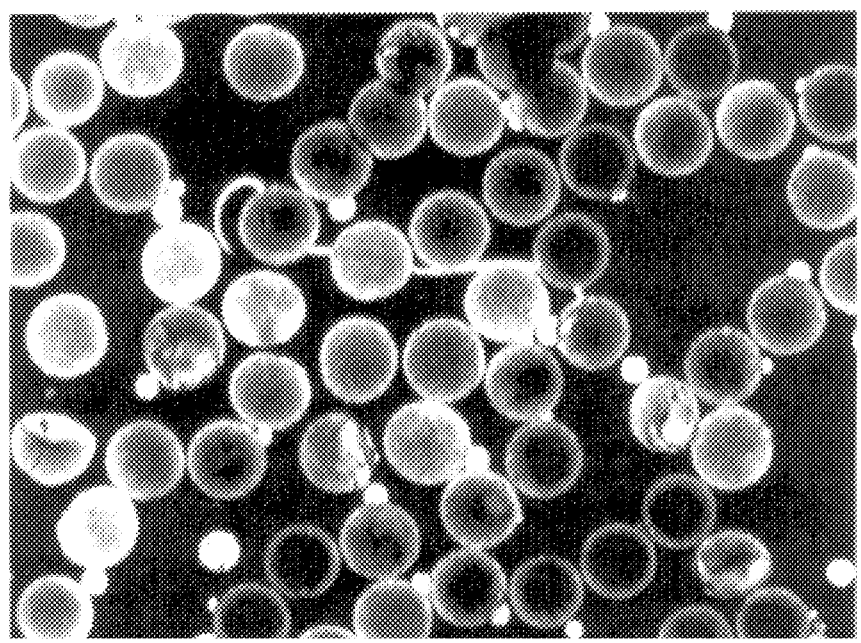
FIG. 14 is a photomicrograph of a dextromethorphan product prepared in accordance with the present invention.

The spinning head was run at 3300 rpm and the temperature raised until the feedstock was processed as a liquiform. Spheres appeared as two major size groups, one at the 40 to 80 micron range and another group at the 160–200 micron range. These two groups were very uniform in shape and many spheres showed small crystalline particles encapsulated within them. The product was very clean and have been shown in the photomicrograph at 50 magnification in FIG. 14.

Example X

Dextromethorphan-Pseudoephedrine Amalgam

In this example, a cough and cold treatment was produced by preparing an amalgam from pseudoephedrine and dextromethorphan. Shearlite particles were made from the two active ingredients. Dextromethorphan HBr and pseudoephedrine HCl were mixed with Myverol 18-06 in amounts which provided 12.5% dextromethorphan, 25% pseudoephedrine, and 62.5% Myverol. The active agents were mixed and then added to Myverol after which they were blended. The blend was then subjected to liquiflash processing at 3300 rpm in an apparatus shown in FIGS. 4A–C.

Figure 15:
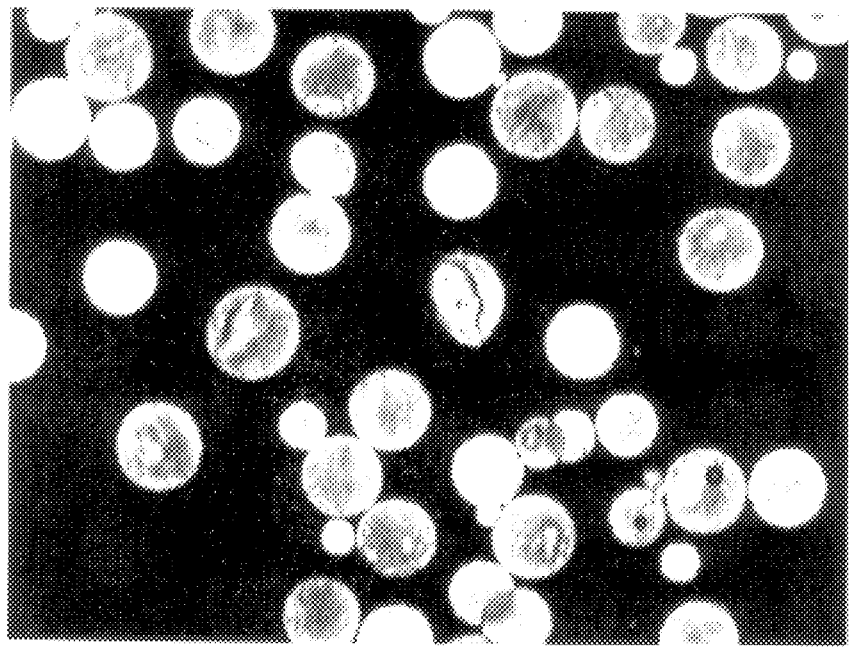
FIG. 15 is a photomicrograph taken at 50 magnification of amalgam of shearlite particles containing a cough and cold treatment formed in accordance with the present invention.

The product was a shearlite particle very uniform in shape and size. Two size groups were produced, one between 20 and 80 microns and another between 120 and 220 microns. A photomicrograph of the product is shown in FIG. 15.

The product was an excellent amalgam which can be used as a cough and cold medicinal treatment.

Example XI

Chloropheniramine-Diphenhydramine-Pseudoephredine Amalgam

In this example, the active ingredients were combined to provide another cough and cold treatment medicament. In particular, chloropheniramine maleate was combined at a rate of 2.8% with 17.5% diphenhydramine HCl and 21% pseudoephredine HCl in combination with 58.7% Myverol 18-06. The active ingredients were blended and then mixed with Myverol and again blended.

Figure 16:
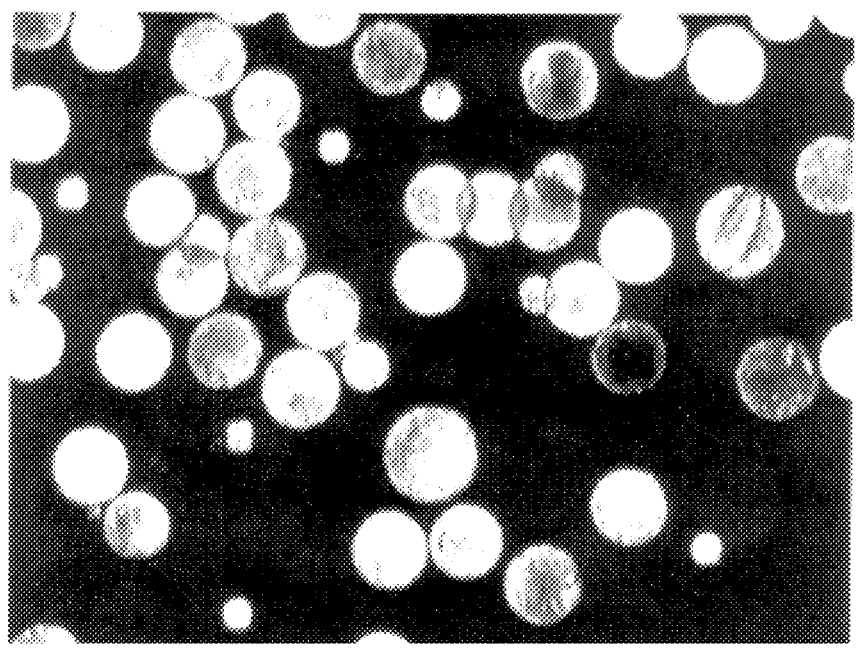
FIG. 16 is a photomicrograph taken at 50 magnification of spheres formed from an amalgam of three (3) active ingredients (also a cough and cold treatment) in accordance with the present invention.

The resulting mixture was liquiflash processed in an apparatus such as that shown in FIGS. 4A–C at 3300 rpm. Photomicrographs of the products produced in accordance with this example are shown in FIG. 16.

Excellent shearlite particles were produced with the combination of the three drugs. Two major size ranges were produced, one at 40–80 microns and another at 160–220 microns.

This example shows that true amalgams can be formed of different active ingredients to provide medicinal treatments to suit the medical practitioner. Furthermore, coatings can be provided as desired in accordance with the present invention. Thus, controlled-release and taste masking can be effected by coating the shearlite particles.

Example XII

Taste Comparison of Coated Unprocessed Ibuprofen and Coated Processed Ibuprofen

Raw ibuprofen feedstock was coated with Ethocel™ brand ethylcellulose:PVP blend at 90:10 ratio. The coating were deposited at a rate of 10% coating. Furthermore, ibuprofen shearlite particles prepared as set forth in Example IV were also coated at a rate of 10% coating with Ethocel™ brand coating.

Products resulting from both coating procedures were then subjected to a taste panel to determine whether or not effective taste masking had been accomplished. In a comparison between the two products, it was found that the raw ibuprofen was not effectively taste masked, while the processed ibuprofen had a high degree of taste masking.

Moreover, upon microscopic inspection, it was seen that the coating on unprocessed ibuprofen was uneven, whereas the processed ibuprofen was evenly coated with a thin coating of the Ethocel™ brand coating.

Therefore, it can be seen that active agents converted to shearlite particles by being subjected to liquiflash conditions provide a excellent substrate for applying coating which masks the unappealing taste of the active agent.

Example XIII

Demonstration of Enhanced Flowability

Experiments were also conducted to demonstrate the enhanced flowability resulting from subjecting a feedstock material to liquiflash processing.

In one method, a flow rate test was conducted by using a funnel having a set diameter of 20 millimeters at the outlet thereof. A measured weight of raw feedstock, i.e, 30 grams, was poured into the funnel while blocking the outlet side. The flow was then timed upon unblocking the outlet. The active ingredients used in the test were acetaminophin and ibuprofen.

Shearlite particles of both ingredients were prepared using the apparatus shown in FIGS. 4A–C. The ibuprofen was processed using 80% ibuprofen, 15% Compritol 888 ATO and 5% Gelucire. Acetaminophin was processed without the addition of other ingredients.

The unprocessed ibuprofen and acetaminophin did not flow from the exit opening of the funnel even after administering tapping on the side of the funnel.

Both the ibuprofen and the acetaminophine which had been processed under liquiflash conditions, however, exit the opening of the funnel. The ibuprofen formula required one tap on the top of the funnel and the entire 30 grams emptied in only one second. The processed acetaminophin required no tapping on the funnel and passed through the exit opening of the funnel in less than one second.

Thus, the present invention can be seen to be highly effective in improving the flow characteristic of active ingredients.

Example XIV

Further Demonstration of Improved Low Characteristic

In this example raw active agent and shearlite particles were tested to compare improvement of the angle of repose. Thus, the ability of the raw material to flow was directly compared to the flowability of the shearlite particle resulting from the present invention.

The method used to measure the angle of repose is a fixed cone method. Reference: "Multi-Particle Oral Drug Delivery," Isaac Ghebre-Sellassie, Vol. 65, Marcel Dekker, Inc., New York. In this method, powder is dropped through a funnel at a controlled distance from a dish which has vertical sides. The powder is poured until it just touches the tip of the funnel. The radius of the powder circle in the dish and the height to the tip of the funnel are measured. The comparison test were run by clamping a funnel 14 millimeters above the bottom of the glass petri dish. The angle of repose is then calculated using the following equation Tan $\phi = h/r$ or $\phi = \text{Arctan } h/r$.

The results of the test indicated that only the shearlite particles of acetaminophine and ibuprofen flowed through the funnel and therefore possess a measurable angle of repose. The angle of repose is also very low, i.e., less than 45°.

The results of the flow test have been set forth hereinbelow in the angle of repose table.

| Material | Flow Rate | Angle of Repose |
|---|---|---|
| Processed APAP | less then 1 second | 19.53° |
| 100% Non-Processed APAP | No Flow | NA |
| Processed Ibuprofen | 1 second | 22.93° |
| Unprocessed Ibuprofen | No Flow | NA |
| 100% Ibuprofen Drug Unprocessed | No Flow | NA |

It can be seen that the process of the present invention provides an active ingredient with significantly enhanced flow characteristic. Basically, it converts non-flowable material to flowable material and improves flowability where there is little or no flow capability.

Thus, while there have been described what are presently believed to be the preferred embodiments of the present invention, those skilled in the art will appreciate that other and further modifications can be made without departing from the true spirit of the invention, and it is intended to include all other such modifications and changes as come within the scope of the invention as set forth in the appended claims.

What is claimed:

1. A medicament comprising monodispersed microspheres of an active agent, each of said microspheres having a solid spherical body with substantially no discontinuity therethrough and having active agent substantially evenly distributed throughout, wherein at least about 80% of the particles have a largest diameter of 60% of the mean diameter and the mean particle size is not greater than 500 microns.

2. The medicament of claim 1 wherein said active agent is selected from the group of active agents consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, antiemetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, $H_2$-antagonists, anti-uricemic drugs and mixtures thereof.

3. The medicament of claim 1 containing up to 100% active agent.

4. The medicament of claim 3 containing pure active agent.

5. Discrete particles comprising:
  monodispersed solid microspheres of heat sensitive material having a smooth spherical surface and substantially no discontinuity therethrough, and having a mean particle size of not greater than 500 microns prepared by
  a) subjecting a solid heat sensitive organic feedstock optionally containing at least one active ingredient and capable of being transformed to liquiform in the substantial absence of dissolving medium, to liquiflash conditions, which transform said feedstock from a solid to a liquid to a solid in less than five (5) seconds, said liquid characterized as having substantially unimpeded internal flow, and
  b) imparting shear force against flowing feedstock resulting from step "a)" in an amount sufficient to separate discrete particles by natural mass separation of said flowing feedstock in the presence of shear force impinging thereon while in said unimpeded-flow condition, wherein any active ingredient is substantially evenly distributed throughout the particles and wherein at least about 80% of the particles have a largest diameter of 60% of the mean diameter and the mean particle size is not greater than 500 microns.

6. The particles of claim 5 wherein said liquiflash conditions are provided by spinning said feedstock in a spinning head having a peripheral barrier provided with heating capability which delivers sufficient energy to said feedstock to liquify it instantaneously and with exit openings for passage of flowing feedstock therethrough in the presence of centrifugal force provided by spinning said head.

7. The particles of claim 6 wherein said shear force is imparted to said flowing feedstock by the resistance of ambient atmosphere against said flowing feedstock as it exits said spinning head.

8. The particles of claim 5 wherein said discretized separated particles are cooled upon exiting said spinning head.

9. The particles of claim 5 wherein said feedstock comprises a medicament.

10. The particles of claim 9 wherein said medicament is an amalgam of two or more active agents.

11. The particles of claim 10 wherein said amalgam comprises cough and cold treatment.

12. The particles of claim 9 wherein said particles have a flowability characteristic which provide an angle of repose not greater than 45°.

13. The particles of claim 9 wherein said medicament is selected from the group of active agents consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, antiemetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, $H_2$-antagonists, anti-uricemic drugs and mixtures thereof.

14. The particles of claim 13 wherein said active agent is a non-steroidal anti-inflammatory agent selected from the group consisting of: tenidap, oxicams and agents containing derivatives of salicylic acid, acetic acid, propionic acid or fenamic acid.

15. The particles of claim 14 wherein said non-steroidal anti-inflammatory agent contains a derivative of propionic acid and is selected from the group consisting of ibuprofen, ketoprofen, flurbiprofen and naproxen.

16. The particles of claim 13 wherein said medicament is the analgesic acetaminophen.

17. The particles of claim 13 wherein said medicament is an $H_2$-antagonist.

18. Coated particles comprising:
  1) monodispersed solid microspheres of heat sensitive material having a smooth spherical surface and substantially no discontinuity therethrough, and having a mean particle size of not greater than 500 microns prepared by
    a) subjecting a solid heat sensitive organic feedstock optionally containing at least one active ingredient and capable of being transformed to liquiform in the substantial absence of dissolving medium, to liquiflash conditions, which transform said feedstock from a solid to a liquid to a solid in less than five (5) seconds, said liquid characterized as having substantially unimpeded internal flow, and
    b) imparting shear force against flowing feedstock resulting from step "a)" in an amount sufficient to separate discrete particles by natural mass separation of said flowing feedstock in the presence of shear force impinging thereon while in said unimpeded-flow condition, wherein any active ingredient is substantially evenly distributed throughout the particles; and
  2) at least one coating of a substance selected from the group consisting of controlled release and taste masking substances and wherein at least about 80% of the particles have a largest diameter of 60% of the mean diameter and the mean particle size is not greater than 500 microns.

19. The new particle of claim 18 wherein said feedstock comprises a saccharide-based material.

20. The new particle of claim 19 wherein said saccharide-based feedstock comprises a sugar.

21. The new particle of claim 18 wherein a combination of active agent is provided in one of said at least one coating, said particle, and a combination thereof to provide a cough and cold treatment.

22. The new particle of claim 18 wherein said at least one coating is selected from the group consisting of a medicament, an antidote, a controlled-release substance, a taste-altering substance, and combinations thereof.

23. The new particle of claim 18 wherein said at least one coating comprises at least one of fats, emulsifiers, and combinations thereof.

24. The new particle of claim 18 wherein said particles have a flowability characteristic which provides an angle of repose of not greater than 45°.

25. The new particle of claim 18 wherein said feedstock comprises a medicament.

26. The new particle of claim 25 wherein said at least one coating is selected from the group consisting of a medicament, an antidote, a controlled-release substance, a taste-altering substance, and combinations thereof.

27. The new particle of claim 25 wherein said at least one coating comprises at least one of fats, emulsifiers, and combinations thereof.

28. The new particle of claim 25 wherein said medicament is selected from the group of active agents consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithromobotic drugs, hypnotics, antiemetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, $H_2$-antagonists, anti-uricemic drugs and mixtures thereof.

29. The new particle of claim 28 wherein said medicament is the analgesic acetaminophen.

30. The new particle of claim 28 wherein said medicament is an $H_2$—antagonist.

31. The new particle of claim 28 wherein said medicament is an amalgam of two or more active agents.

32. The new particle of claim 31 wherein said amalgam comprises a cough and cold treatment.

33. The new particle of claim 28 wherein said medicament is a non-steroidal anti-inflammatory agent selected from the group consisting of salicylates, acetic acids, propionic acids, fenamates, oxicams, and tenidap.

34. The new particle of claim 33 wherein said non-steroidal anti-inflammatory agent is selected from the group consisting of ibuprofen, ketoprofen, flurbiprofen, and naproxen.

* * * * *